United States Patent
Ogura et al.

(10) Patent No.: US 6,332,869 B1
(45) Date of Patent: Dec. 25, 2001

(54) SUPERIOR-AND-INFERIOR-LIMB BLOOD-PRESSURE INDEX MEASURING APPARATUS

(75) Inventors: Toshihiko Ogura, Inuyama; Tomohiro Nunome, Komaki, both of (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/560,575

(22) Filed: Apr. 27, 2000

(30) Foreign Application Priority Data

May 7, 1999 (JP) .................................................. 11-126861
Jun. 1, 1999 (JP) .................................................. 11-153565

(51) Int. Cl.[7] ...................................................... A61B 5/02
(52) U.S. Cl. ............................ 600/490; 600/492; 600/497
(58) Field of Search ..................................... 600/490, 485, 600/481, 492, 493, 494, 495, 496, 497, 498, 499, 500, 503

(56) References Cited

U.S. PATENT DOCUMENTS

| | | | |
|---|---|---|---|
| 5,101,828 | * | 4/1992 | Welkowitz et al. ................... 600/481 |
| 5,265,011 | * | 11/1993 | O'Rourke .............................. 600/485 |
| 5,715,826 | * | 2/1998 | Horrocks et al. ..................... 600/485 |
| 5,743,857 | * | 4/1998 | Shinoda et al. ....................... 600/496 |

FOREIGN PATENT DOCUMENTS 2 281 782 A   3/1995 (GB) .
03 162827   7/1991 (JP) .
1003125   6/1997 (NL) .

* cited by examiner

Primary Examiner—Robert L. Nasser
Assistant Examiner—Navin Natnithithadha
(74) Attorney, Agent, or Firm—Oliff & Berridge PLC

(57) ABSTRACT

An apparatus for measuring a superior-and-inferior-limb blood-pressure ("BP") index of a living subject, including an inferior-limb BP measuring device which includes a first inflatable cuff adapted to be wound around an inferior limb of the subject and which measures an inferior-limb BP value of the subject based on a first pulse wave obtained while a first pressure of the first cuff is changed, a superior-limb BP measuring device which includes a second inflatable cuff adapted to be wound around a superior limb of the subject and which measures a superior-limb BP value of the subject based on a second pulse wave obtained while a second pressure of the second cuff is changed, a cuff-pressure changing device which changes the first and second pressures of the first and second cuffs, such that a time when the first pressure being changed becomes equal to an estimated inferior-limb BP value coincides with a time when the second pressure being changed becomes equal to an estimated superior-limb BP value, and an index determining device for determining the BP index of the subject, based on the inferior-limb and superior-limb BP values measured by the inferior-limb and superior-limb BP measuring devices while the first and second pressures of the first and second cuffs are changed by the cuff-pressure changing device.

7 Claims, 12 Drawing Sheets

SUPERIOR-AND-INFERIOR-LIMB BLOOD-PRESSURE INDEX MEASURING APPARATUS

BACKGROUND OF THE INVENTION

1. Field of the Invention

The present invention relates to an apparatus for measuring a superior-and-inferior-limb blood-pressure index of a living subject (e.g., a ratio of an inferior-limb blood pressure to a superior-limb blood pressure, or a ratio of a superior-limb blood pressure to an inferior-limb blood pressure).

2. Related Art Statement

For a person who suffers arterial obstruction or arteriostenosis, his or her inferior-limb blood pressure ("BP") value should be lower than his or her corresponding superior-limb BP value (f or example, a systolic superior-limb BP value corresponds to a systolic inferior-limb BP value). Meanwhile, if an inferior-limb BP value of a person is higher than his or her corresponding superior-limb BP value by a certain value, he or she may suffer aortic incompetence or aortitis syndrome limited to aortic arch. It has been practiced to utilize these facts for diagnosing arterial disease based on a ratio of an inferior-limb BP value to a superior-limb BP value, or a ratio of a superior-limb BP value to an inferior-limb BP value, i.e., a superior-and-inferior-limb blood-pressure index.

Generally, the above superior-and-inferior-limb blood-pressure index (hereinafter, abbreviated to the "SIL BP index") is obtained or calculated as the ratio of a systolic BP value of an ankle as the inferior-limb BP value to a systolic BP of an upper arm as the superior-limb BP value, that is, ankle brachial index (abbreviated to "ABI") or ankle/arm BP index (abbreviated to "AAI" or "API"). If a measured ankle/arm BP index of a living person is smaller than a threshold, e.g., about 0.9, abnormality may be diagnosed on the person. Thus, even a small change of the inferior-limb or superior-limb BP value greatly affects the diagnosis.

The BP of a living person can change even in a short time. For example, the BP of a living person at rest can physiologically change by more than 20 mmHg in ten seconds. Therefore, if there is a time difference between a first time when a systolic BP is measured from an inferior limb and a second time when a systolic BP is measured from a superior limb, the BP of the person may change during the time difference. However, the conventional SIL BP index measuring device cannot enable an observer to judge, when there is a difference between an inferior-limb BP value and a superior-limb BP value, whether that difference is caused by the timewise BP change of the person or by the fact that the two BP values are measured from the different body portions of the person. Thus, the accuracy of the superior-and-inferior-limb blood-pressure index determined based on the two BP values is not sufficiently high.

SUMMARY OF THE INVENTION

It is therefore an object of the present invention to provide a superior-and-inferior-limb blood-pressure ("SIL BP") index measuring apparatus which can measure a highly accurate SIL BP index value of a person.

The Applicants have carried out various studies and have found that if a time when an inferior-limb BP value is measured coincides with a time when a superior-limb BP value is measured, it can be judged that the difference between the inferior-limb BP value and the superior-limb BP value is caused by only the fact that the two BP values are measured from the different body portions of the person. The present invention has been developed based on this finding.

(1) According to a first feature of the present invention, there is provided an apparatus for measuring a superior-and-inferior-limb blood-pressure index of a living subject, comprising an inferior-limb blood-pressure measuring device which includes a first inflatable cuff adapted to be wound around an inferior limb of the subject, and which measures an inferior-limb blood pressure of the subject based on a first pulse wave obtained while a first pressing pressure of the first cuff is changed; a superior-limb blood-pressure measuring device which includes a second inflatable cuff adapted to be wound around a superior limb of the subject, and which measures a superior-limb blood pressure of the subject based on a second pulse wave obtained while a second pressing pressure of the second cuff is changed; a cuff-pressure changing device which changes the first and second pressing pressures of the first and second cuffs, such that a time when the first pressing pressure being changed becomes equal to an estimated inferior-limb blood pressure coincides with a time when the second pressing pressure being changed becomes equal to an estimated superior-limb blood pressure; and index determining means for determining the superior-and-inferior-limb blood-pressure index of the subject, based on the inferior-limb and superior-limb blood pressures measured by the inferior-limb and superior-limb blood-pressure measuring devices while the first and second pressing pressures of the first and second cuffs are changed by the cuff-pressure changing device.

According to this feature, the cuff-pressure changing device changes the first and second pressing pressures of the first and second cuffs, such that the time when the first pressing pressure being changed becomes equal to the estimated inferior-limb blood pressure coincides with the time when the second pressing pressure being changed becomes equal to the estimated superior-limb blood pressure. While the cuff-pressure changing device changes the first and second pressing pressures of the first and second cuffs in this way, the inferior-limb and superior-limb blood pressures are measured by the inferior-limb and superior-limb blood-pressure measuring devices, respectively. The index determining means determines the superior-and-inferior-limb blood-pressure index of the subject, based on the thus measured inferior-limb and superior-limb blood pressures. Therefore, the present apparatus can provide highly accurate superior-and-inferior-limb blood-pressure index values.

(2) According to a second feature of the present invention that includes the first feature (1), the apparatus further comprises estimated-inferior-limb-blood-pressure determining means for operating, before the cuff-pressure changing device changes the first and second pressing pressures of the first and second cuffs, the inferior-limb blood-pressure measuring device to measure an inferior-limb blood pressure of the subject, and determining the measured inferior-limb blood pressure as the estimated inferior-limb blood pressure; and estimated-superior-limb-blood-pressure determining means for operating, before the cuff-pressure changing device changes the first and second pressing pressures of the first and second cuffs, the superior-limb blood-pressure measuring device to measure a superior-limb blood pressure of the subject, and determining the measured superior-limb blood pressure as the estimated superior-limb blood pressure.

According to this feature, the estimated-inferior-limb-blood-pressure determining means operates, before the cuff-pressure changing device changes the first and second pressing pressures of the first and second cuffs, the inferior-limb blood-pressure measuring device to measure an inferior-limb blood pressure of the subject, and determines the thus measured inferior-limb blood pressure as the estimated inferior-limb blood pressure, and the estimated-superior-limb-blood-pressure determining means operates, before the cuff-pressure changing device changes the first and second pressing pressures of the first and second cuffs, the superior-limb blood-pressure measuring device to measure a superior-limb blood pressure of the subject, and determines the thus measured superior-limb blood pressure as the estimated superior-limb blood pressure. Therefore, the present apparatus can assure that the time when the inferior-limb blood pressure to be used to determine the blood-pressure index is measured accurately coincides with the time when the superior-limb blood pressure to be used to determine the blood-pressure index is measured. Thus, the present apparatus can provide more highly accurate blood-pressure index values.

(3) According to a third feature of the present invention that includes the second feature (2), the estimated-inferior-limb-blood-pressure determining means and the estimated-superior-limb-blood-pressure determining means comprise means for operating, before the cuff-pressure changing device changes the first and second pressing pressures of the first and second cuffs, the inferior-limb and superior-limb blood-pressure measuring devices to measure the inferior-limb and superior-limb blood pressures of the subject while changing the first and second pressing pressures of the first and second cuffs such that the first and second pressing pressures are kept substantially equal to each other.

According to this feature, before the cuff-pressure changing device changes the first and second pressing pressures of the first and second cuffs, the inferior-limb and superior-limb blood-pressure measuring devices are operated to measure the inferior-limb and superior-limb blood pressures of the subject while changing the first and second pressing pressures of the first and second cuffs such that the first and second pressing pressures are kept substantially equal to each other. Therefore, the inferior-limb and superior-limb blood pressures are measured at respective times which are considerably near to each other. This contributes to minimizing the influence of the measurement-time difference to the difference between the estimated inferior-limb blood pressure and the estimated inferior-limb blood pressure. Thus, the present apparatus can more reliably assure that the time when the inferior-limb blood pressure is measured accurately coincides with the time when the superior-limb blood pressure is measured.

(4) According to a fourth feature of the present invention that includes any one of the first to third features (1) to (3), the index determining means comprises means for determining, as the superior-and-inferior-limb blood-pressure index, a ratio of the inferior-limb blood pressure to the superior-limb blood pressure, or a ratio of the superior-limb blood pressure to the inferior-limb blood pressure.

(5) According to a fifth feature of the present invention that includes any one of the first to fourth features (1) to (4), the cuff-pressure changing device comprises adjusting means for adjusting at least one of a first time when decreasing of the first pressing pressure of the first cuff is started and a second time when decreasing of the second pressing pressure of the second cuff is started, so that the time when the first pressing pressure being decreased becomes equal to the estimated inferior-limb blood pressure coincides with the time when the second pressing pressure being decreased becomes equal to the estimated superior-limb blood pressure.

(6) According to a sixth feature of the present invention that includes the fifth feature (5), the adjusting means comprises means for adjusting at least one of a first time when increasing of the first pressing pressure of the first cuff is started and a second time when increasing of the second pressing pressure of the second cuff is started, so that the time when the first pressing pressure being decreased becomes equal to the estimated inferior-limb blood pressure coincides, with the time when the second pressing pressure being decreased becomes equal to the estimated superior-limb blood pressure.

(7) According to a seventh feature of the present invention that includes any one of the first to fourth features (1) to (4), the cuff-pressure changing device comprises adjusting means for adjusting at least one of a first pressure at which decreasing of the first pressing pressure of the first cuff is started and a second pressure at which decreasing of the second pressing pressure of the second cuff is started, so that the time when the first pressing pressure being decreased becomes equal to the estimated inferior-limb blood pressure coincides with the time when the second pressing pressure being decreased becomes equal to the estimated superior-limb blood pressure.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
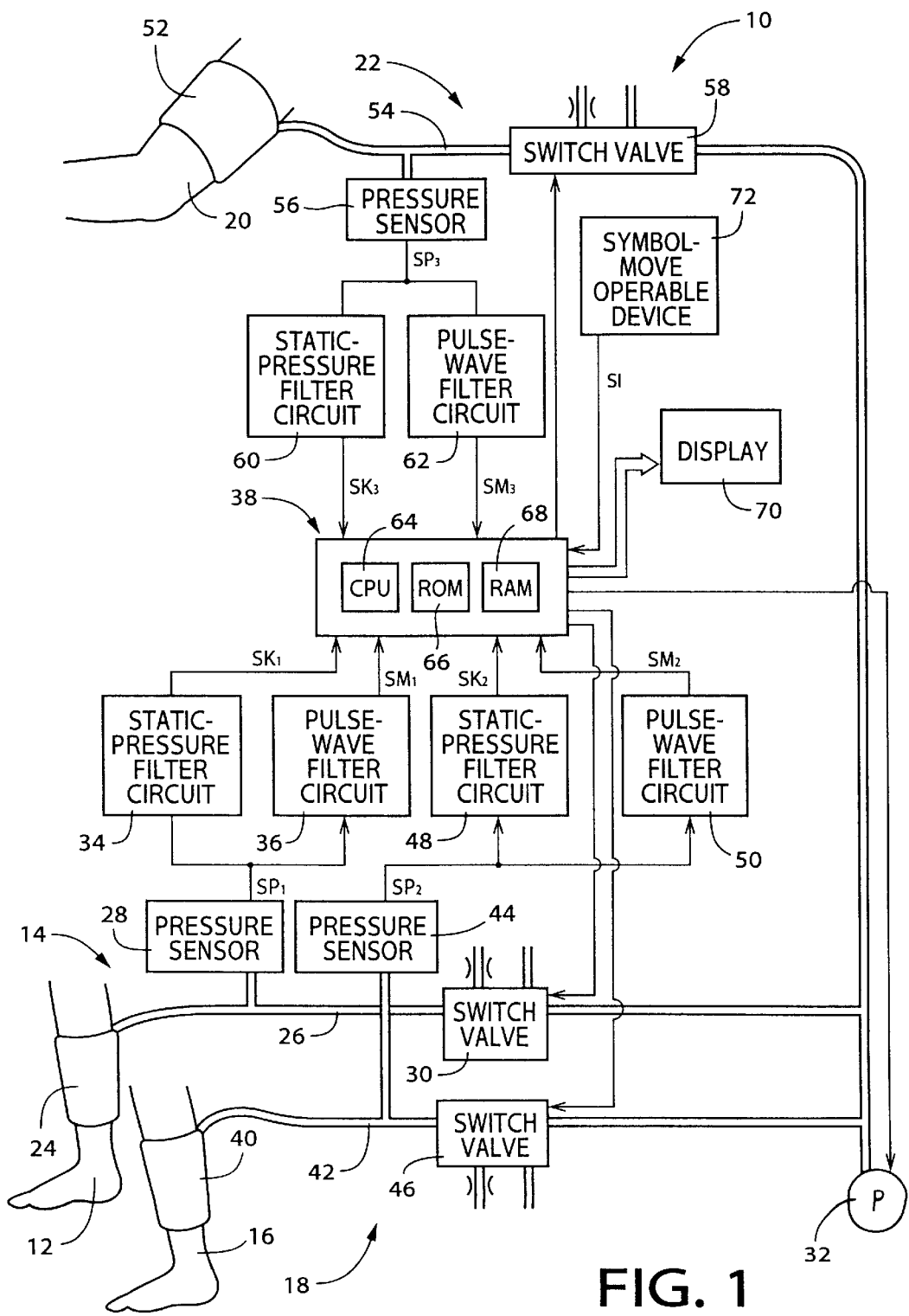
FIG. 1 is a diagrammatic view of the construction of an ankle/arm blood-pressure ("BP") index measuring apparatus to which the present invention is applied.

Hereinafter, there will be described an ankle/arm blood-pressure ("BP") index measuring apparatus 10 to which the present invention is applied, by reference to the drawings. FIG. 1 is a diagrammatic view showing the construction of the measuring apparatus 10. The ankle/arm BP index measuring apparatus 10 is a sort of superior-and-inferior-limb "SIL") BP index measuring apparatus, since the measuring apparatus 10 measures, as an inferior-limb BP value, a BP value from an ankle of a patient as a living person and measures, as a superior-limb BP value, a BP value from an upper arm of the patient. The present apparatus 10 carries out the BP measurements on the patient who takes the face-down, lateral, or face-up position so that the upper arm and the ankle are substantially level with each other.

In FIG. 1, the ankle/arm BP index measuring apparatus 10 includes a right-leg first BP measuring device 14 which measures a BP value from a right ankle 12 of the patient, a left-leg first BP measuring device 18 which measures a BP value from a left ankle 16 of the patient, and a second BP measuring device 22 which measures a BP value from an upper arm 20 of the patient.

The right-leg first BP measuring device 14 includes an inflatable cuff 24 which includes a belt-like cloth bag and a rubber bag accommodated in the cloth bag and which is wound around the right ankle 12 of the patient; a piping 26; and a pressure sensor 28, an electrically-operated switch valve 30, and an air pump 32 which are connected to the cuff 24 via the piping 26. The switch valve 30 is selectively placed in one of three operation states, that is, (a) a pressurized-air-supply state in which the switch valve 30 allows pressurized air to be supplied from the air pump 32 to the cuff 24, (b) a slow-deflation state in which a degree of opening of the switch valve 30 is so controlled as to allow the pressurized air to be deflated slowly at an arbitrary rate from the cuff 24, and (c) a quick-deflation state in which the switch valve 30 allows the pressurized air to be deflated quickly from the cuff 24.

The pressure sensor 28 detects an air pressure in the cuff 24, and supplies a pressure signal, $SP_1$, representing the detected air pressure, to a static-pressure filter circuit 34 and a pulse-wave filter circuit 36. The static-pressure filter circuit 34 includes a low-pass filter which allows only low frequencies to pass therethrough and thereby selects, from the pressure signal $SP_1$, a cuff-pressure signal, $SK_1$, representing a cuff pressure, $P_{C1}$, as the constant component of the detected air pressure. The filter circuit 34 supplies the cuff-pressure signal $SK_1$ to an electronic control device 38 via an analog-to-digital ("A/D") converter (not shown).

The pulse-wave filter circuit 36 includes a band-pass filter which allows only specific frequencies to pass therethrough and thereby selects, from the pressure signal $SP_1$, a pulse-wave signal, $SM_1$, representing a pulse wave as the oscillatory component of the detected air pressure. The filter circuit 36 supplies the pulse-wave signal $SM_1$ to the control device 38 via an A/D converter (not shown). The pulse-wave signal $SM_1$ represents a right-leg first pulse wave, $M1_R$, produced from an artery (i.e., a posterior tibial artery) of the right ankle 12 that is pressed by the cuff 24, and the pulse-wave filter circuit 36 functions as one of two first pulse-wave sensors.

The left-leg first BP measuring device 18 includes an inflatable cuff 40, a piping 42, a pressure sensor 44, and a switch valve 46 which have respective constructions identical with those of the counterparts 24, 26, 28, 30 of the right-leg first BP measuring device 14. The switch valve 46 is connected to the air pump 32. The pressure sensor 44 detects an air pressure in the cuff 40, and supplies a pressure signal, $SP_2$, representing the detected air pressure, to a static-pressure filter circuit 48 and a pulse-wave filter circuit 50 which have respective constructions identical with those of the counterparts 34, 36 of the right-leg first BP measuring device 14. The static-pressure filter circuit 48 selects, from the pressure signal $SP_2$, a cuff-pressure signal, $SK_2$, representing a cuff-pressure, $P_{C2}$, as the constant component of the detected air pressure, and supplies the cuff-pressure signal $SK_2$ to the control device 38 via an A/D converter (not shown). The pulse-wave filter circuit 50 selects, from the pressure signal $SP_2$, a pulse-wave signal, $SM_2$, representing a pulse wave as the oscillatory component of the detected air pressure, and supplies the pulse-wave signal $SM_2$ to the control device 38 via an A/D converter (not shown). The pulse-wave signal $SM_2$ represents a left-leg first pulse wave, $M1_L$, produced from an artery (i.e., a posterior tibial artery) of the left ankle 16 that is pressed by the cuff 40, and the pulse-wave filter circuit 50 functions as the other of the two first pulse-wave sensors.

The second BP measuring device 22 includes an inflatable cuff 52 which has a construction identical with the cuff 24 or 40 and which is wound around an upper arm 20 (e.g., a right upper arm) of the patient; and a piping 54, a pressure sensor 56, and a switch valve 58 which have respective constructions identical with those of the counterparts 24, 26, 28, 30 of the right-leg first BP measuring device 14. The switch valve 58 is connected to the air pump 32. The pressure sensor 56 detects an air pressure in the cuff 52, and supplies a pressure signal, $SP_3$, representing the detected air pressure, to a static-pressure filter circuit 60 and a pulse-wave filter circuit 62 which have respective constructions identical with those of the counterparts 34, 36 of the right-leg first BP measuring device 14. The static-pressure filter circuit 60 selects, from the pressure signal $SP_3$, a cuff-pressure signal, $SK_3$, representing a cuff pressure, $P_{C3}$, as the constant component of the detected air pressure, and supplies the cuff-pressure signal $SK_3$ to the control device 38 via an A/D converter (not shown). The pulse-wave filter circuit 62 selects, from the pressure signal $SP_3$, a pulse-wave signal, $SM_3$, representing a pulse wave as the oscillatory component of the detected air pressure, and supplies the pulse-wave signal $SM_3$ to the control device 38 via an A/D converter (not shown). The pulse-wave signal $SM_3$ represents a second pulse wave, M2, produced from an artery (i.e., a brachial artery) of the upper arm 20 that is pressed by the cuff 52, and the pulse-wave filter circuit 62 functions as a second pulse-wave sensor.

The electronic control device 38 is essentially provided by a microcomputer including a central processing unit ("CPU") 64, a read only memory ("ROM") 66, a random access memory ("RAMS") 68, and an input-and-output ("I/O") port (not shown), and processes input signals according to control programs pre-stored in the ROM 66, while utilizing the temporary-storage function of the RAM 68. The control device 38 outputs, from the I/O port, drive signals to the air pump 32 and the three switch valves 30, 46, 58 to control the respective operations thereof, and display signals to a display device 70 to control the contents displayed thereby.

A symbol-move operable device 72 includes a first button or member which is operable by an operator to move a symbol, displayed on the display device 70, in a leftward direction, and a second button or member which is operable by the operator to move the symbol in a rightward direction. Alternatively, the operable device 72 may employ a dial which is rotatable by an operator in opposite directions. The operable device 72 produces a symbol-move signal, SI, representing an amount of operation of each of the first and second buttons, or an amount, and a direction, of rotation of the dial, and supplies the signal SI to the control device 38. For example, each time the first or second button is pushed, the operable device 72 may produce one signal SI to move the symbol by a unit distance in a corresponding one of the leftward and rightward directions, and for a time duration when the first or second button is continuously pushed, the device 72 may continue producing signals SI to move continuously the symbol in a corresponding one of the leftward and rightward directions. Thus, the operable device 72 produces the symbol-move signal or signals SI representing the amount of operation of each of the first and second buttons, or the amount and direction of rotation of the dial.

Figure 2:
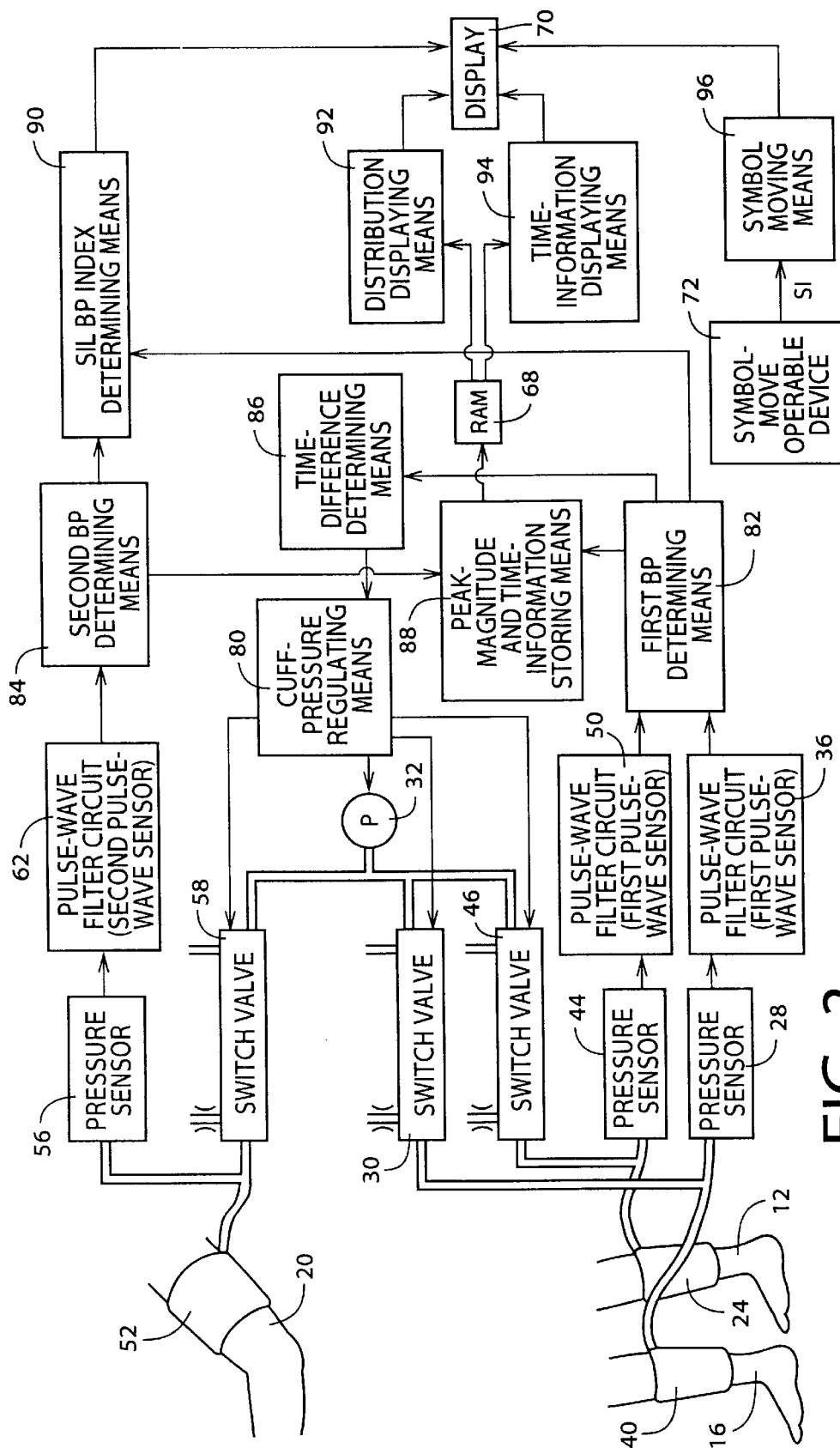
FIG. 2 is a diagrammatic view of important control functions of an electronic control device of the measuring apparatus of FIG. 1.

FIG. 2 is a diagrammatic view for explaining the important control functions of the control device 38. In an initial-time BP measuring operation, the cuff-pressure regulating means 80 controls the air pump 32, and simultaneously controls the three switch valves 30, 46, 58 that are connected to the air pump 32, so that the respective pressing pressures of the three cuffs 24, 40, 52 are quickly increased up to a predetermined target pressure value, $P_{CM}$, (e.g., about 180 mmHg) and then are slowly decreased at a rate of about 3 mmHg/sec. In a second-time BP measuring operation, the regulating means 80 controls, like the initial-time BP measuring operation, the air pump 32 and the three switch valves 30, 46, 58 connected thereto, so that the respective pressing pressures of the three cuffs 24, 40, 52 first are quickly increased up to a predetermined target pressure value $P_{CM}$ and then are slowly decreased at a rate of about 3 mmHg/sec. However, the regulating means 80 controls, based on time differences, $\Delta t_{cb}$, $\Delta t_{ca}$, determined by time-difference calculating means 86, described later, the three switch valves 30, 46, 58 to start decreasing the respective air pressures of the three cuffs 24, 40, 52 at such respective timings which should assure that a time when a right-leg first systolic BP value, $BP1_{RSYS}$, as a first systolic BP value of the right ankle 12 is measured by the right-leg first BP measuring device 14, a time when a left-leg first systolic BP value, $BP1_{LSYS}$, as a first systolic BP value of the left ankle 16 is measured by the left-leg first BP measuring device 18, and a time when a second systolic BP value, BP2, of the upper arm 20 is measured by the second BP measuring device 22, coincide with one another.

A first BP determining means 82 determines respective magnitudes (i.e., amplitudes) $P1_R$ of respective peaks of heartbeat-synchronous pulses of the right-leg first pulse wave $M1_R$ represented by the pulse-wave signal $SM_1$ obtained by the pulse-wave filter circuit 36 when the air pressure of the cuff 24 wound around the right ankle 12 is slowly decreased by the cuff-pressure regulating means 80, and determines right-leg first BP values, $BP1_R$, as BP values of the right ankle 12, according to well-known oscillometric method, based on the timewise change of the thus determined respective peak magnitudes $P1_R$. In addition, the first BP determining means 82 determines respective magnitudes (i.e., amplitudes) $P1_L$ of respective peaks of heartbeat-synchronous pulses of the left-leg first pulse wave $M1_L$ represented by the pulse-wave signal $SM_2$ obtained by the pulse-wave filter circuit 50 when the air pressure of the cuff 40 wound around the left ankle 16 is slowly decreased by the cuff-pressure regulating means 80, and determines left-leg first BP values, $BP1_L$, as BP values of the left ankle 16, according to the oscillometric method, based on the timewise change of the thus determined respective peak magnitudes $P1_L$. The right-leg first BP values $BP1_R$ include a systolic BP value $BP1_{RSYS}$ and a diastolic BP value $BP1_{RDIA}$, and the left-leg first BP values $BP1_L$ include a systolic BP value $BP1_{LSYS}$ and a diastolic BP value $BP1_{LDIA}$. Hereinafter, when it is not needed to distinguish the right-leg first BP values $BP1_R$ and the left-leg first BP values $BP1_L$ from each other, those BP values will be wholly referred to as the first BP values BP1.

A second BP determining means 84 determines respective magnitudes (i.e., amplitudes) P2 of respective peaks of heartbeat-synchronous pulses of the second pulse wave M2 represented by the pulse-wave signal $SM_3$ obtained by the pulse-wave filter circuit 62 when the air pressure of the cuff 52 wound around the upper arm 20 is slowly decreased by the cuff-pressure regulating means 80, and determines second BP values, BP2, (systolic BP value $BP2_{SYS}$ and diastolic BP value $BP2_{DIA}$) of the upper arm 20, according to the oscillometric method, based on the timewise change of the thus determined respective peak magnitudes P2.

A time-difference determining means 86 determines, as a cuff al one of the three cuffs 24, 40, 52 that has earliest measured, in the initial-time BP measuring operation, a BP value (i.e., one of a systolic BP value $BP_{SYS}$, a mean BP value $BP_{MEAN}$, and a diastolic BP value $BP_{DIA}$ that is used by an ankle/arm BP index determining means 90, described later), determines, as a cuff b, another of the three cuffs 24, 40, 52 that has second earliest measured a BP value, and determines, as a cuff c, the third one of the three cuffs 24, 40, 52 that has last measured a BP value. The time-difference determining means 86 additionally determines a time difference, $\Delta t_{cb}$, between a time, $t_c$, when the cuff c measured the BP value and a time, $t_b$, when the cuff b measured the BP value, and a time difference, $\Delta t_{ca}$, between the time $t_c$ and a time, $t_a$, when the cuff a measured the BP value. During the initial-time BP measuring operation, the respective instantaneous pressures of the three cuffs 24, 40, 52 continue to be equal to one another, and accordingly the BP value determined by the cuff a is the highest and the BP value determined by the cuff c is the lowest.

A peak-magnitude and time-information storing means 88 sequentially stores, in the RAM 68, the respective peak magnitudes $P1_R$, $P1_L$ of the heartbeat-synchronous pulses of each of the first pulse waves $M1_R$, $M1_L$ (i.e., the pulse-wave signals $SM_1$, $SM_2$) that are determined by the first BP determining means 82, and respective first time information representing respective first times when the heartbeat-synchronous pulses of each of the first pulse waves $M1_R$, $M1_L$ are detected by a corresponding one of the pulse-wave filter circuits 36, 50. In addition, the peak-magnitude and time-information storing means 88 sequentially stores, in the RAM 68, the respective peak magnitudes P2 of the heartbeat-synchronous pulses of the second pulse wave M2 (i.e., the pulse-wave signal $SM_3$) that are determined by the second BP determining means 84, and respective second time information representing respective second times when the heartbeat-synchronous pulses of the second pulse wave M2 are detected by the pulse-wave filter circuit 62. The first times include a time when the first BP value BP1 is measured, and the second times include a time when the second BP value BP2 is measured. Each first or second time information represents a time, t, that elapses from a reference time, e.g., a time when each BP measuring operation is started, or a time when the slow cuff deflation is started, or a parameter corresponding, one by one, to the time t. The parameter may be the instantaneous cuff pressure $P_C$ in the case where the three cuffs 24, 40, 52 are slowly deflated at the same rate.

The ankle/arm BP index determining means 90 determines or calculates an ankle/arm BP index value ("API") based on the first BP value BP1 determined by the first BP determining means 82 and the corresponding second BP value BP2 determined by the second BP determining means 88 (e.g., the systolic first BP value $BP1_{SYS}$ corresponds to the systolic second BP value $BP2_{SYS}$, and the diastolic first BP value $BP1_{DIA}$ corresponds to the diastolic second BP value $BP2^{DIA}$). For example, the API may be obtained by dividing the first BP value BP1 by the corresponding second BP value BP2, or dividing the second BP value BP2 by the corresponding second BP value BP1.

A distribution displaying means 92 displays, in a first two-dimensional graph having a time-information axis representing first time information and a first-peak-magnitude axis representing first peak magnitude, a distribution of respective first peak magnitudes P1 of heartbeat-synchronous pulses of the first pulse wave M1 detected in the second-time BP measuring operation, which magnitudes are stored in the RAM 68 by the peak-magnitude and time-information storing means 88, along the time-information axis, and additionally displays, in a second two-dimensional graph which has the time-information axis and a second-peak-magnitude axis representing second peak magnitude, a distribution of respective second peak magnitudes P2 of heartbeat-synchronous pulses of the second pulse wave M2 detected in the second-time BP measuring operation, which magnitudes are stored in the RAM 68 by the storing means 88, along the time-information axis.

A time-information displaying means 94 displays, along the time-information axis of the first two-dimensional graph in which the first distribution is displaced by the distribution displaying means 92, a first symbol representing the first time information which is stored in the RAM 68 by the peak-magnitude and time-information storing means. 88 and which represents the first time when the first BP value BP1 is measured by the first BP measuring device 14 or 18, and additionally displays, along the time-information axis of the second two-dimensional graph in which the second distribution is displaced, a second symbol representing the second time information which is stored in the RAM 68 and which represents the second time when the second BP value BP2 is measured by the second BP measuring device 22. The first and second BP values are used by the ankle/arm BP index determining means 90 to determine the ankle/arm BP index value.

A symbol moving means 96 moves, based on the symbol-move signal SI supplied from the symbol-move operable device 72, one of the two symbols displayed by the time-information displaying means 94, relative to the other symbol, along the time-information axis of a corresponding one of the first and second two-dimensional graphs.

Figure 3:
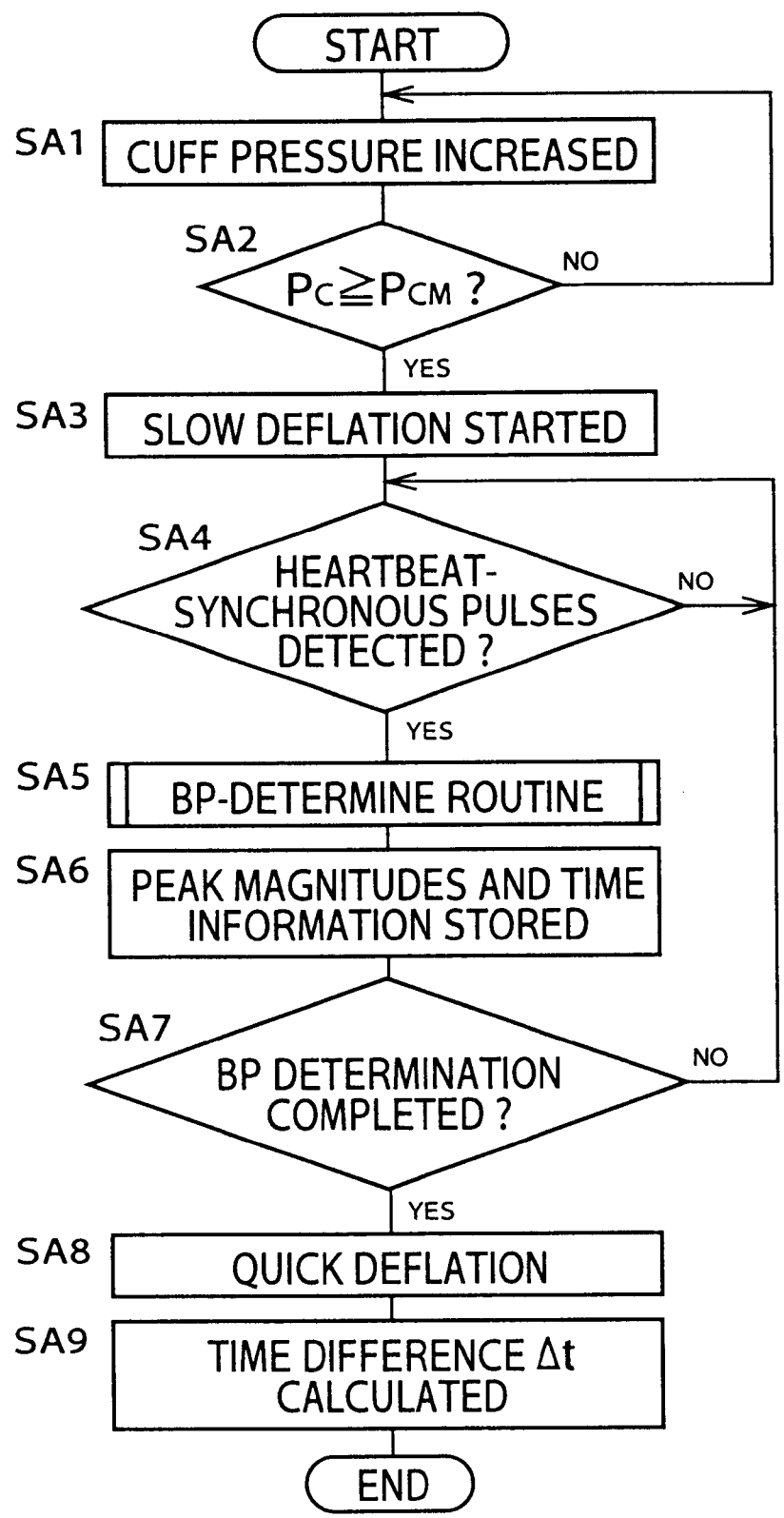
FIG. 3 is a flow chart representing an initial-time BP-measure routine according to which the control device of the measuring apparatus of FIG. 1 is operated to carry out an initial-time BP measuring operation.
Figure 4:
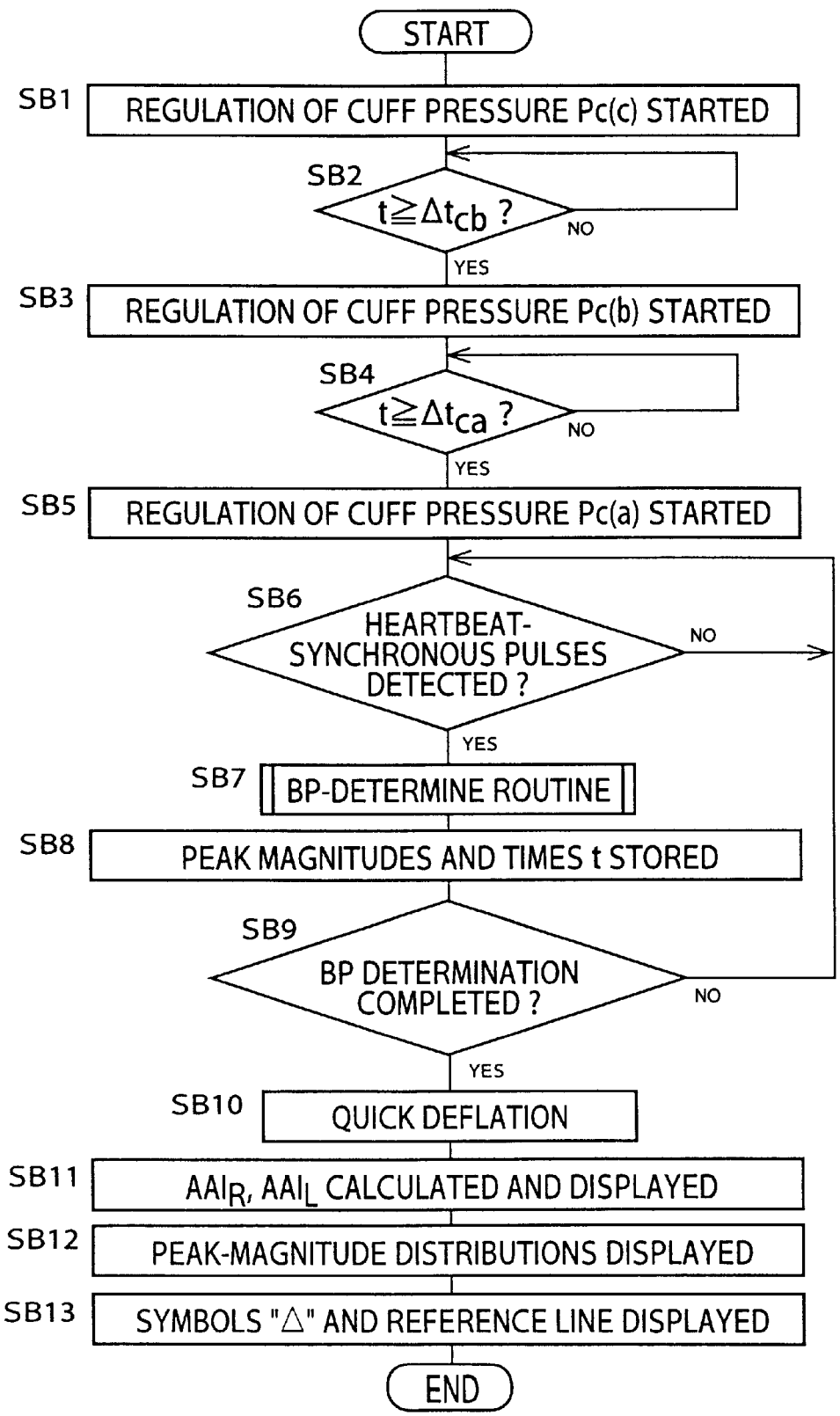
FIG. 4 is a flow chart representing a second-time BP-measure routine according to which the control device of the measuring apparatus of FIG. 1 is operated to carry out a second-time BP measuring operation.
Figure 5:
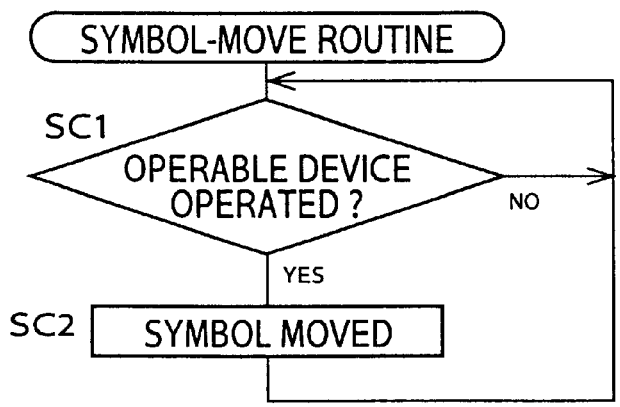
FIG. 5 is a flow chart representing a symbol-move routine according to which the control device of the measuring apparatus of FIG. 1 is operated to move a symbol which is displayed by a display device in the second-time BP measuring operation.

FIGS. 3, 4, and 5 are flow charts representing control programs according to which the control device 38 is operated. FIG. 3 shows the flow chart representing the initial-time BP-measure routine; FIG. 4 shows the flow chart representing the second-time BP-measure routine; and FIG. 5 shows the flow chart representing the symbol-move routine according to which one of the two symbols displayed in the second-time BP measuring operation is moved.

First, the control device 38 carries out Steps SA1, SA2, and SA3 of FIG. 3 corresponding to the cuff-pressure regulating means 80. At Step SA1, the three switch valves 30, 46, 58 are simultaneously switched to their pressure-supply positions and the air pump 32 is operated, so that the respective air pressures of the three cuffs 24, 40, 52 are quickly increased. At Step SA2, it is judged whether al, the air pressures $P_C$ of the three cuffs 24, 40, 52 have reached the predetermined target pressure value $P_{CM}$ (about 180 mmHg). If a negative judgment is made at Step SA2, Steps SA1 and SA2 are repeated to continue increasing the air pressures $P_C$ of the cuffs 24, 40, 52.

If a positive judgment is made at Step SA2, the control goes to Step SA3 to stop the operation of the air pump 32 and simultaneously switch the three switch valves 30, 46, 58 to their slow-deflation positions, so that the respective air pressures $P_C$ of the three cuffs 24, 40, 52 are decreased slowly at a predetermined low rate of about 3 mmHg/sec.

Step SA3 is followed by Step SA4 to read in the pulse-wave signals $SM_1$, $SM_2$, $SM_3$ supplied from the pulse-wave filter circuits 36, 50, 62 and judge whether the three filter circuits have detected respective one heartbeat-synchronous pulses of the three pulse waves $M1_R$, $M1_L$, M2. If a negative judgment is made at Step SA4, the control device 38 repeats Step SA4. Meanwhile, if a positive judgment is made, the control of the control device goes to the BP-determine routine of Step SA5, corresponding to the first BP determining means 82 and the second BP determining means 84. More specifically described, the control device 38 determines a magnitude $P1_R$ of a peak of the detected one heartbeat-synchronous pulse of the right-leg first pulse wave $M1_R$, a magnitude $P1_L$ of a peak of the detected one heartbeat-synchronous pulse of the left-leg first pulse wave M1$_R$, and a magnitude P2 of a peak of the detected one heartbeat-synchronous pulse of the second pulse wave M2. In addition, the control device determines a right-leg first systolic BP value BP1$_{RSYS}$, etc. based on the time-wise change of the determined peak magnitudes P1$_R$ according to a well-known oscillometric BP-determine algorithm. Similarly, the control device 38 determines a left-leg first systolic BP value BP1$_{LSYS}$, etc. based on the time-wise change of the determined peak magnitudes P1$_L$ according to the oscillometric BP-determine algorithm, and determines a second systolic BP value BP2$_{SYS}$, etc. based on the time-wise change of the determined peak magnitudes P2 according to the oscillometric BP-determine algorithm. Moreover, the control device 38 stores, in the RAM 68, not only the thus determined BP values, but also respective rates of change of the cuff pressures P$_C$ of the three cuffs 24, 40, 52 connected to the three switch valves 30, 46, 58. Those rates of change of cuff pressures P$_C$ of the three cuffs 24, 40, 52 are defined by respective degrees of opening of the three switch valves 30, 46, 58, respectively.

Step SA5 is followed by Step SA6 corresponding to the peak-magnitude and time-information storing means 88. At Step SA6, the control device 38 stores, in predetermined memory areas of the RAM 68, the peak magnitudes P1$_R$, P1$_L$, P2 determined at Step SA5 for the respective one heartbeat-synchronous pulses of the pulse waves M1$_R$, M1$_L$, M2 detected at Step SA4, and respective times when the respective one heartbeat-synchronous pulses of the pulse waves M1$_R$, M1$_L$, M2 are detected.

Step SA6 is followed by Step SA7 to judge whether the three BP measuring devices 14, 18, 22 have measured or determined respective diastolic BP values at Step SA5. While a negative judgment is made at Step SA7, Steps SA4 to SA7 are repeated to determine, for respective one heartbeat-synchronous pulses of the three pulse waves M1$_R$, M1$_L$, M2, respective peak magnitudes P1$_R$, P1$_L$, P2 thereof, and repeat the BP-determine routine of Step SA5 based on the respective updated timewise changes of the peak magnitudes P1$_R$, P1$_L$, P2. In addition, the control device 38 iteratively stores the determined peak magnitudes P1$_R$, P1$_L$, P2 and the times when the heartbeat-synchronous pulses of the three pulse waves M1$_R$, M1$_L$, M2 are detected. Those times are substantially equal to respective times when the peak magnitudes P1$_R$, P1$_L$, P2 of the heartbeat-synchronous pulses of the three pulse waves M1$_R$, M1$_L$, M2 are determined.

If a positive judgment is made at Step SA7, the control of the control device 38 goes to Step SA8 corresponding to the cuff-pressure regulating means 80. At Step SA8, the three switch valves 30, 46, 58 are switched to their quick-deflation positions, so that the respective air pressures of the three cuffs 24, 40, 52 are quickly decreased.

Step SA8 is followed by Step SA9 corresponding to the time-difference determining means 86. At Step SA9, the control device 38 determines, as the cuff a1 one of the three cuffs 24, 40, 52 that has earliest measured or determined the corresponding systolic BP value BP$_{SYS}$ at Step SA5, determines, as the cuff b, another of the three cuffs 24, 40, 52 that has second earliest measured the corresponding systolic BP value BP$_{SYS}$, and determines, as the cuff c, the third one of the three cuffs 24, 40, 52 that has last measured the corresponding systolic BP value BP$_{SYS}$. In addition, the control device 38 determines a time difference $\Delta t_{cb}$ between a time t$_c$ when the cuff c measured the systolic BP value BP$_{SYS}$ and a time t$_b$ when the cuff b measured the systolic BP value BP$_{SYS}$, and a time difference $\Delta t_{ca}$ between the time t$_c$ and a time t$_a$ when the cuff a measured the systolic BP value BP$_{SYS}$.

If the patient is free of the inferior-limb arterial disease, the first systolic BP value BP1$_{SYS}$ of the right or left ankle 12 or 16 will be higher than the second systolic BP value BP1$_{SYS}$ of the upper arm 20. In this case, therefore, the cuff 24 or 40 wound around the right or left ankle 12 or 16 will be determined as the cuff a1 and the cuff 52 wound around the upper arm 20 will be determined as the cuff c.

After quitting the initial-time BP-measure routine of FIG. 3, the control device 38 enters the second-time BP-measure routine of FIG. 4. The routine of FIG. 4 is started a predetermined time (e.g., 10 seconds) after the routine of FIG. 3 is ended.

First, the control device 38 carries out Steps SB1 to SB5 corresponding to the cuff-pressure regulating means 80, by starting regulating the cuff pressure P$_C$ of the cuff c that is estimated to determine last a systolic BP value BP$_{SYS}$, in the three cuffs a, b, c.

At SB1, the control device 38 starts regulating the cuff pressure P$_{C(c)}$ of the cuff c determined at Step SA9. That is, the air pump 32 is operated, and the switch valve connected to the cuff c is switched to its pressure-supply position, so that the cuff pressure P$_{C(c)}$ is increased quickly up to the predetermined target pressure value P$_{CM}$ (e.g., 180 mmHg), and subsequently the switch valve is switched to its slow-deflation position, so that the cuff pressure P$_{C(c)}$ is decreased slowly at a predetermined rate (e.g. 3 mmHg/sec). The degree of opening of the switch valve connected to the cuff c, employed in the second-time BP measuring operation, is determined according to a relationship between the degree of opening of the switch valve and the rate of change of the cuff pressure P$_{C(c)}$, stored in the RAM 68 in the initial-time BP measuring operation.

Step SB1 is followed by Step SB2 to judge whether the time t that is measured from the time when the increasing of the cuff pressure P$_{C(c)}$ is started at Step SB1, has elapsed by the time difference $\Delta t_{cb}$ determined at Step SA9. If a negative judgment is made at Step SB2, Step SB2 is repeated to continue regulating the cuff pressure P$_{C(c)}$ only.

Meanwhile, if a positive judgment is made at Step SB2, the control of the control device 38 goes to Step SB3 to start regulating the cuff pressure P$_{C(b)}$ of the cuff b, like the cuff c. That is, the switch valve connected to the cuff b is switched to its pressure-supply position, so that the cuff pressure P$_{C(b)}$ is increased quickly up to the predetermined target pressure value P$_{CM}$, and subsequently the switch valve is switched to its slow-deflation position, so that the cuff pressure P$_{C(b)}$ is decreased slowly at the same rate as that at which the cuff pressure P$_{C(c)}$ is decreased. The degree of opening of the switch valve connected to the cuff b, used in the second-time BP measuring operation, is determined based on the rate of change of the cuff pressure P$_{C(c)}$, according to a relationship between the degree of opening of the switch valve and the rate of change of the cuff pressure P$_{C(b)}$, stored in the RAM 68 in the initial-time BP measuring operation.

Step SB3 is followed by Step SB4 to judge whether the time t has elapsed by the time difference $\Delta t_{ca}$ determined at Step SA9. If a negative judgment is made at Step SB4, Step SB3 is repeated to continue regulating the cuff pressure P$_{C(c)}$ and the cuff pressure P$_{C(b)}$.

Figure 6:
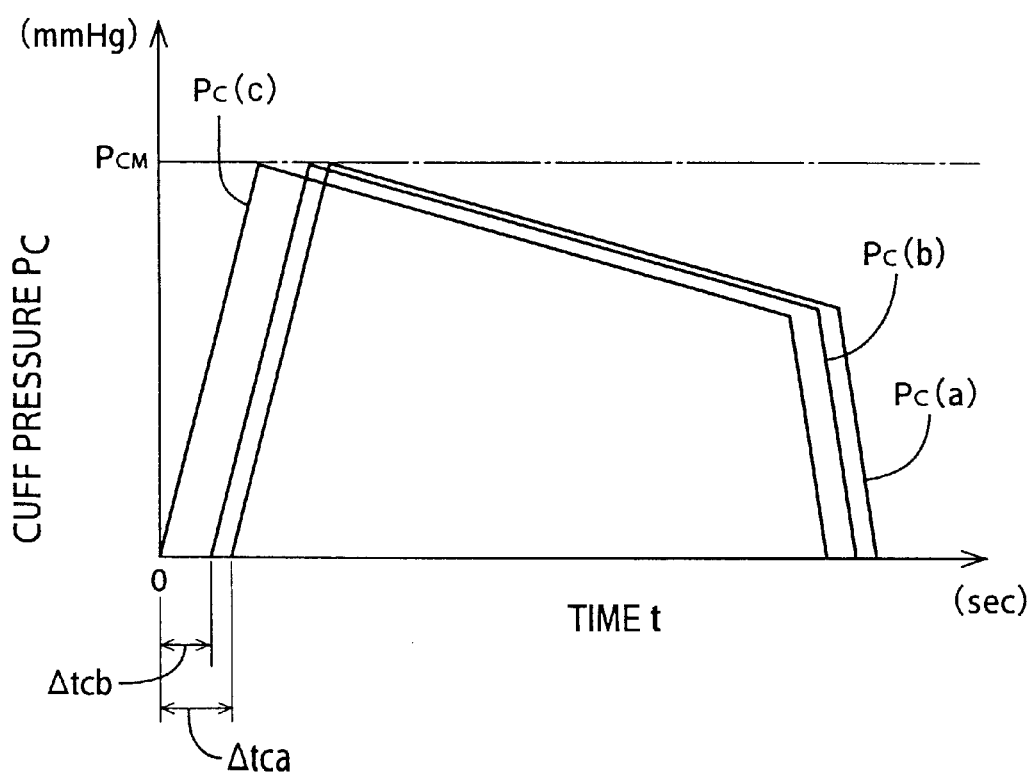
FIG. 6 is a graph showing respective changes of respective air pressures, $P_C$, of three inflatable cuffs of the measuring apparatus of FIG. 1, with respect to time, t, in the second-time BP measuring operation.

Meanwhile, if a positive judgment is made at Step SB4, the control goes to Step SB4 to start regulating the cuff pressure P$_{C(a)}$ of the cuff a1 like the cuffs c, b. That is, the switch valve connected to the cuff a is switched to its pressure-supply position, so that the cuff pressure P$_{C(a)}$ is increased quickly up to the predetermined target pressure value $P_{CM}$, and subsequently the switch valve is switched to its slow-deflation position, so that the cuff pressure $P_{C(c)}$ is decreased slowly at the same rate as that at which the cuff pressures $P_{C(c)}$, $P_{C(b)}$ are decreased. The degree of opening of the switch valve connected to the cuff al used in the second-time BP measuring operation, is determined based on the rate of change of the cuff pressure $P_{C(c)}$, according to a relationship between the degree of opening of the switch valve and the rate of change of the cuff pressure $P_{C(a)}$, stored in the RAM 68 in the initial-time BP measuring operation. FIG. 6 shows respective timewise changes of the three cuff pressures $P_{C(c)}$, $P_{C(b)}$, $P_{C(a)}$ that are thus regulated.

Steps SB6 to SB10 are similar to Steps SA4 to SA8 of FIG. 3. That is, at Step SB6, the control device 38 reads in the pulse-wave signals $SM_1$, $SM_2$, $SM_3$ and judge whether the control device 38 have read in respective one heartbeat-synchronous pulses of the first and second pulse waves $M1_R$, $M1_L$, M2. At Step SB7 corresponding to the first and second BP determining means 82, 84, the control device 38 determines respective peak magnitudes $P1_R$, $P1_L$, P2 of the respective one heartbeat-synchronous pulses of the first and second pulse waves $M1_R$, $M1_L$, M2, and determines a right-leg first systolic BP value $BP1_{SYS}$, a left-leg first systolic BP value $BP1_{LSYS}$, a second systolic BP value $BP2_{SYS}$, etc., based on respective timewise changes of the three peak magnitudes $P1_R$, $P1_L$, P2, shown in FIG. 7. At Step SB8 corresponding to the peak-magnitude and time-information storing means 88, the control device 38 stores, in the predetermined memory areas of the RAM 68, the determined peak magnitudes $P1_R$, $P1_L$, P2 of the respective one heartbeat-synchronous pulses of the first and second pulse waves $M1_R$, $M1_L$, M2, and respective times t when the respective heartbeat-synchronous pulses of the first and second pulse waves $M1_R$, $M1_L$, M2 are detected, or when the peak magnitudes $P1_R$, $P1_L$, P2 of the pulses are determined. The times t include a right-leg first time $t_{1R}$ when the right-leg first systolic BP value $BP1_{RSYS}$ is measured; a left-leg first time $t_{1L}$ when the left-leg first systolic BP value $BP1_{LSYS}$ is measured; and a second time $t_2$ when the second systolic BP value $BP2_{SYS}$ is measured. At Step SB9, the control device 38 judges whether the BP determination at Step SB7 has been completed. If a positive judgment is made at Step SB9, the control goes to Step SB10 corresponding to the cuff-pressure regulating means 80, and quickly deflates the three cuffs al b, c.

Step SB10 is followed by Step SB11 corresponding to the ankle/arm BP index determining means 90. At Step SB11, the control device 38 calculates a right ankle/arm BP index value $API_R$ by dividing the right-leg first systolic BP value $BP1_{RSYS}$ determined at Step SB7 by the second systolic BP value $BP2_{SYS}$ determined at Step SB7, and calculates a left-leg ankle/arm BP index value $APeI_L$ by dividing the left-leg first systolic BP value $BP1_{SYS}$ determined at Step SA7 by the second systolic BP value $BP2_{SYS}$. The thus determined right-leg and left-leg ankle/arm BP index values $API_R$, $API_L$ are displayed in digits on the display device 70.

Step SB11 is followed by Step SB12 corresponding to the distribution displaying means 92. At Step SB12, the control device 38 displays, based on the peak magnitudes $P1_R$, $P1_L$, P2 and the times t stored in the RAM 68 at Step SB8, respective distributions of the peak magnitudes $P1_R$, $P1_L$, P2 with respect to the time t, in three two-dimensional graphs 106, 108, 104 having respective time axes 100, 102, 98 each representing the time t. More specifically described, the control device 38 displays, in the fist two-dimensional graph 104 having the time axis 98 and a peak-magnitude axis 110, a distribution of the respective peak magnitudes P2 of the heartbeat-synchronous pulses of the second pulse wave M2 with respect to the time t, displays, in the second graph 106 having the time axis 100 which is parallel to the time axis 98 of the first graph 104 and has the same graduations as those of the time axis 98, and having a peak-magnitude axis 112 located on the same line as that on which the peak-magnitude axis 110 of the first graph 104 is located, a distribution of the respective peak magnitudes $P1_R$ of the heartbeat-synchronous pulses of the right-leg first pulse wave $M1_R$ with respect to the time t, and displays, in the third graph 108 having the time axis 102 which is parallel to the time axes 98, 100 and has the same graduations as those of the time axes 98, 100, and having a peak-magnitude axis 114 located on the same line as that on which the peak-magnitude axes 110, 112 are located, a distribution of the respective peak magnitudes $P1_L$ of the heartbeat-synchronous pulses of the left-leg first pulse wave $M1_L$ with respect to the time t.

Figure 7:
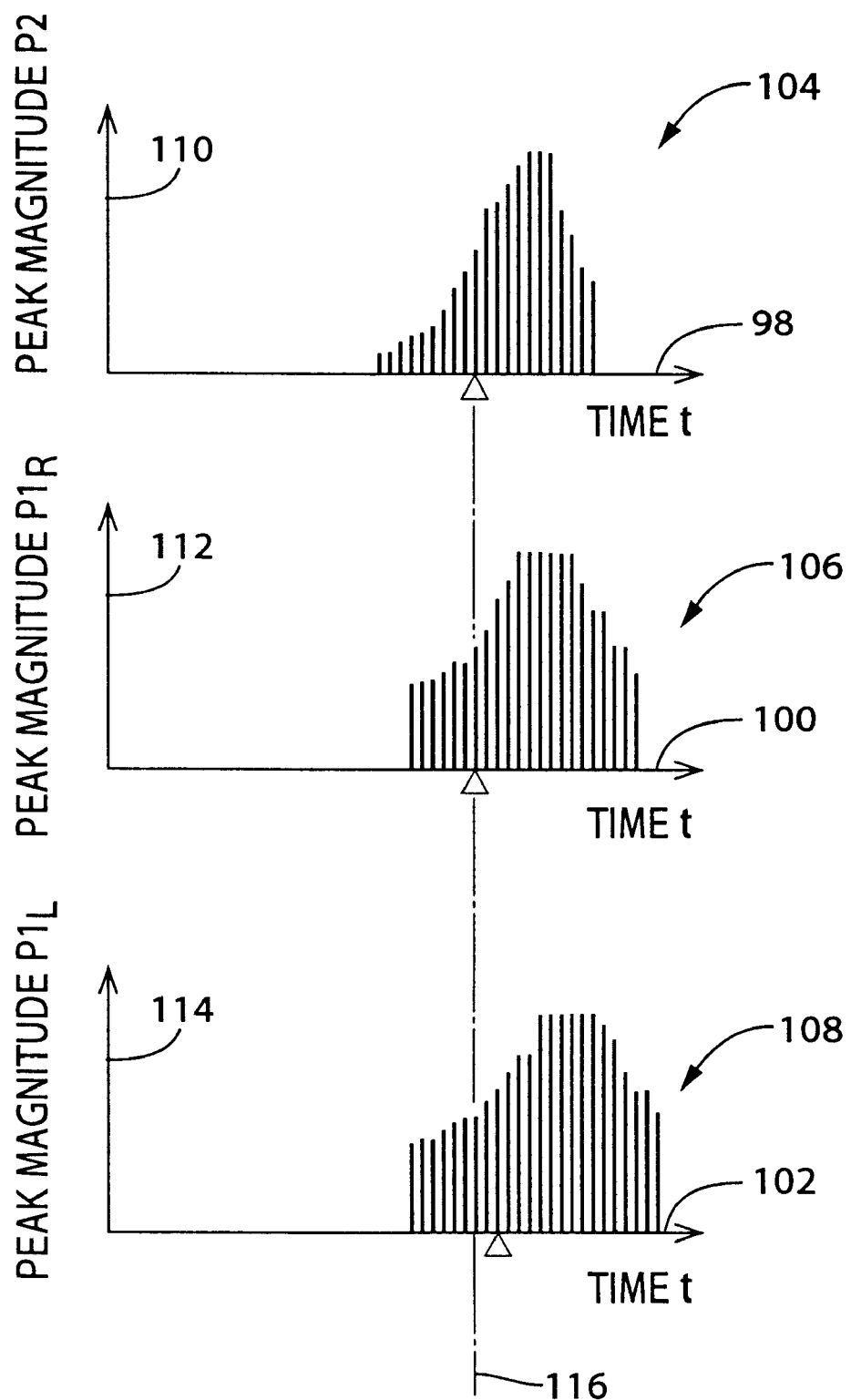
FIG. 7 is three two-dimensional graphs which are displayed by the display device of the measuring apparatus of FIG. 1 and which show a timewise distribution of respective peak magnitudes of heartbeat-synchronous pulses of a second pulse wave, a timewise distribution of respective peak magnitudes of heartbeat-synchronous pulses of a right-leg first pulse wave, and a timewise distribution of respective peak magnitudes of heartbeat-synchronous pulses of a left-leg first pulse wave, respectively.

Step SB12 is followed by Step SB13 corresponding to the time-information displaying means 94. At Step SB13, the control device 38 displays, in the three graphs 104, 106, 108 in which the respective peak-magnitude distributions are displayed at Step SB12, respective symbols "Δ" representing the right-leg first time $t_{1R}$, the left-leg first time $t_{1L}$, and the second time $t_2$ that had been stored at Step SB8, as shown in FIG. 7. In addition, the display device 70 displays a reference line 116 which passes through one of the three symbols "Δ" (e.g., the symbol representing the second time $t_2$, as shown in FIG. 7) and is parallel to the three peak-magnitude axes 110, 112, 114. This reference line 116 is for helping an observer easily recognize the time differences among the first and second times $t_{1R}$, $t_{1L}$, $t_2$.

In the present embodiment, the control device 38 determines, based on the results obtained in the initial-time BP determining operation, the respective timings at which the respective regulations of cuff pressures $P_C$ of the three cuffs 24, 40, 52 are started, so that, in the second-time BP measuring operation, the three BP measuring devices 14, 18, 22 simultaneously measure or determine respective systolic BP values $BP1_{RSYS}$, $BP1_{LSYS}$, $BP2_{SYS}$. However, the three graphs 104, 106, 108 shown in FIG. 7 indicate that the left-leg first systolic BP value $BP1_{LSYS}$ was measured several pulses after the right-leg first and second systolic BP values $BP1_{RSYS}$, $BP2_{SYS}$ were measured. In addition, the observer can judge, from respective tendencies of change of the three peak-magnitude distributions at respective positions indicated by the three symbols "Δ", whether the three systolic BP values $BP1_{RSYS}$, $BP1_{LSYS}$, $BP2_{SYS}$ have been properly measured.

Then, the control device 38 carries out the symbol-move routine of FIG. 5. First, at Step SC1, the control device 38 judges whether the control device 38 has received the symbol-move signal SI from the symbol-move operable device 72. If a negative judgment is made at this step, Step SC1 is repeated. Meanwhile, when the operable device 72 is operated and the control device 38 receives the signal SI from the operable device 72, a positive judgment is made at Step SC1. Then, the control of the control device 38 goes to Step SC2 corresponding to the symbol moving means 96. At Step SC2, the control device 38 moves, along the time axes 100, 102, the respective distributions of the peak magnitudes, $P1_R$, $P1_L$ of the two first pulse waves $M1_R$, $M1_L$ and the two symbols "Δ" representing the two first times $t_{1R}$, $t_{1L}$, by an amount or distance corresponding to the amount or length of the symbol-move signal SI.

As is apparent from the foregoing description, the peak-magnitude and time-information storing means 88 (SB8)

stores, in the RAM 68, the respective peak magnitudes $P1_R$, $P1_L$ of the heartbeat-synchronous pulses of each of the first pulse waves $M1_R$, $M1_L$ detected by the pulse-wave filter circuits 36, 50, and the respective times t when the heartbeat-synchronous pulses of each of the first pulse waves $M1_R$, $M1_L$ are detected by a corresponding one of the pulse-wave filter circuits 36, 50, and additionally stores, in the RAM 68, the respective peak magnitudes P2 of the heartbeat-synchronous pulses of the second pulse wave M2 detected by the pulse-wave filter circuit 62, and the respective times t when the heartbeat-synchronous pulses of the second pulse wave M2 are detected by the pulse-wave filter circuit 62. The distribution displaying means 92 (SB12) displays, based on the peak magnitudes $P1_R$, $P1_L$, P2 and the respective times t stored in the ROM 68, the respective distributions of the peak magnitudes $P1_R$, $P1_L$, P2 of the first and second pulse waves $M1_R$, $M1_L$, M2, each with respect to the time t, in the respective two-dimensional graphs 104, 106, 108 having the respective time axes 98, 100, 102 and the respective peak-magnitude axes 110, 112, 114. The time-information displaying means 94 (SB13) displays, in the graphs 104, 106, 108, the respective symbols representing the respective times t when the respective BP values $BP1_{RSYS}$, $BP1_{LSYS}$, $BP2_{SYS}$ are measured. Therefore, the observer can easily recognize visually the time differences among the respective times t when the respective BP values $BP1_{RSYS}$, $BP1_{LSYS}$, $BP2_{SYS}$ are measured.

In addition, in the present embodiment, the observer or the operator can move, along the time axis 102, the symbol representing the first time t when the left-leg first systolic BP value $BP_l$ is measured, to a position corresponding to a position where the symbol representing the second time t when the second systolic BP value $BP2_{SYS}$ is measured, is indicated along the time axis 98. Judging from the amount of operation of the operable device 72 needed to cause the two symbols to be aligned with each other with respect to the time t, the observer can easily recognize the time difference between the first time when the first BP value $BP1_{LSYS}$ is measured and the second time when the second BP value $BP2_{SYS}$ is measured.

Next, there will be described a second embodiment of the present invention that relates to an ankle/arm BP index measuring apparatus 210, by reference to FIGS. 8 to 13 and FIGS. 14A and 14B.

Figure 8:
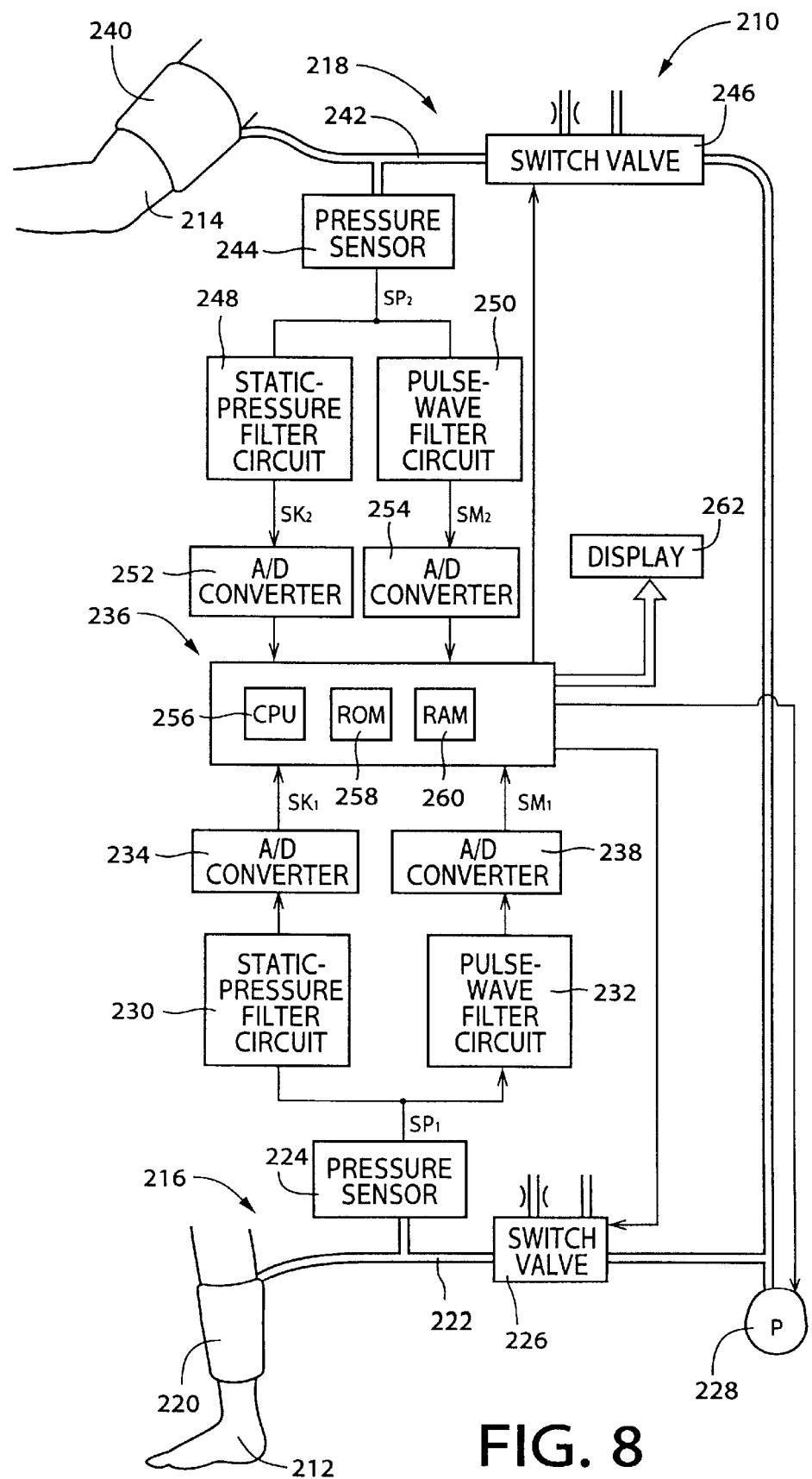
FIG. 8 is a diagrammatic view of the construction of another ankle/arm BP index measuring apparatus as a second embodiment of the present invention.
Figure 9:
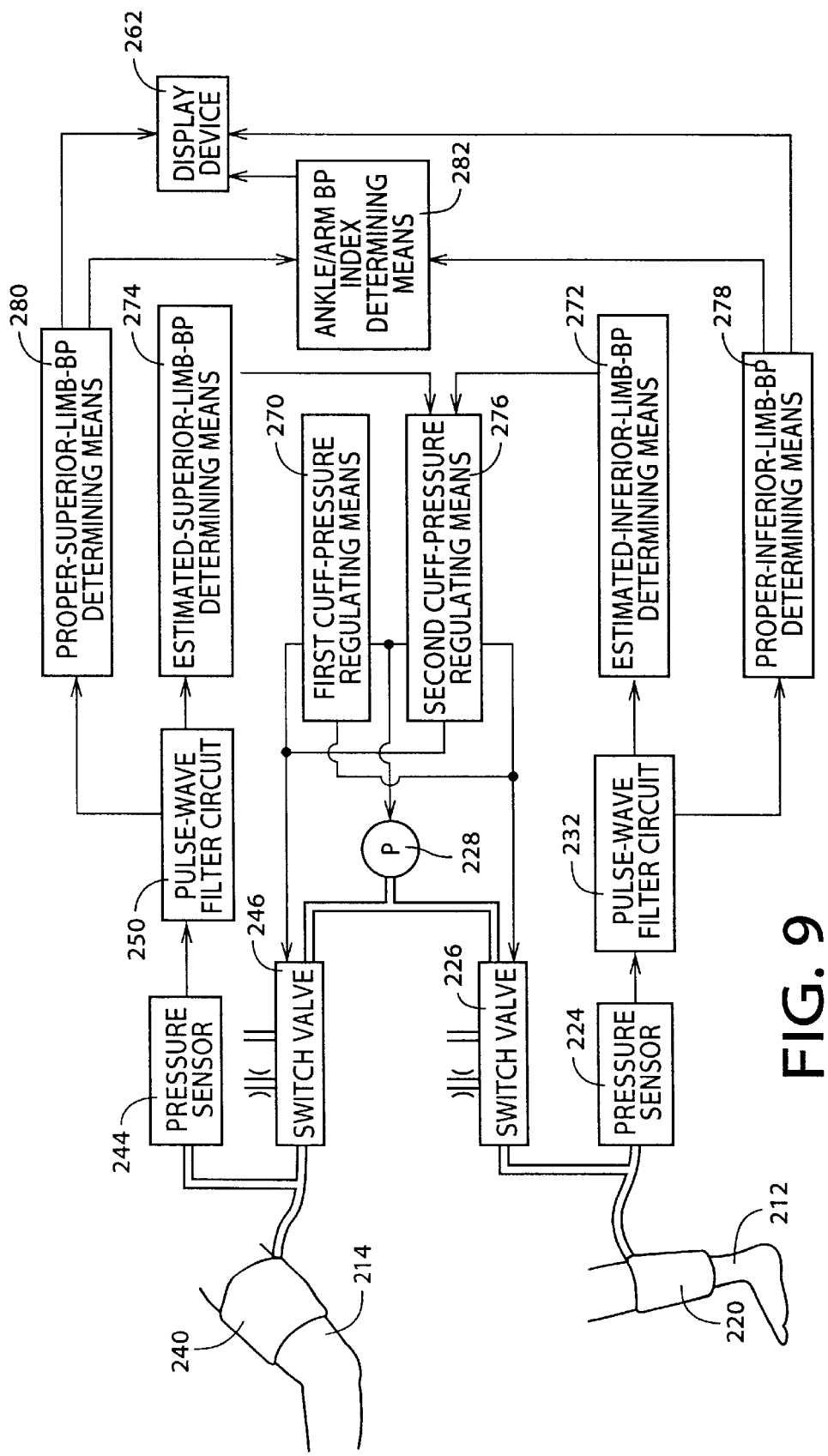
FIG. 9 is a diagrammatic view of important control functions of an electronic control device of the measuring apparatus of FIG. 8.
Figure 10:
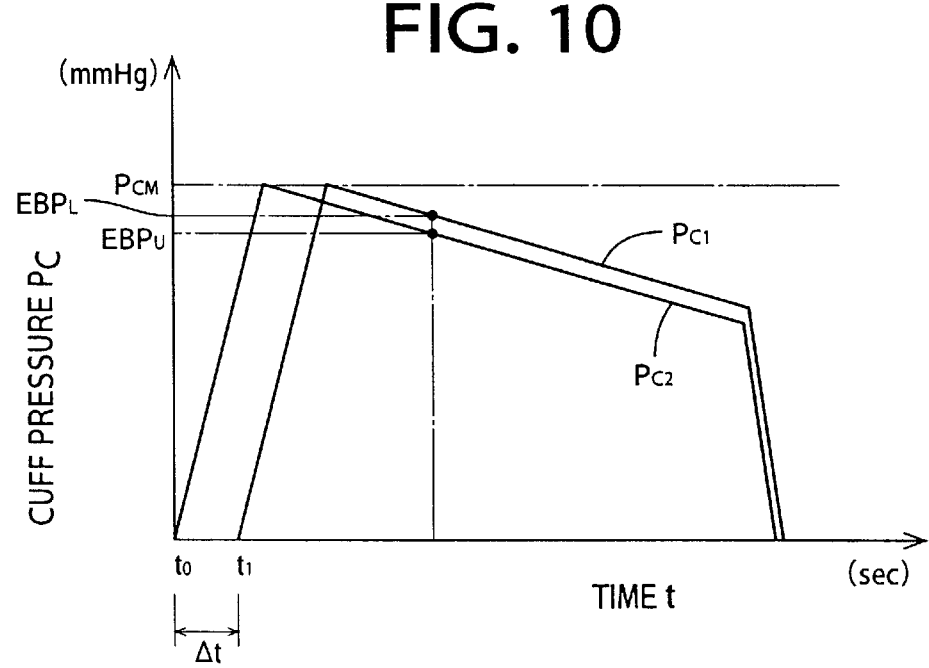
FIG. 10 is a graph showing respective changes of respective air pressures, $P_{C1}$, $P_{C2}$, of two inflatable cuffs of the measuring apparatus of FIG. 8, with respect to time, t, in a second-time BP measuring operation in which respective times when respective increasings of the two air pressures $P_{C1}$, $P_{C2}$ are started, are adjusted relative to each other.
Figure 11:
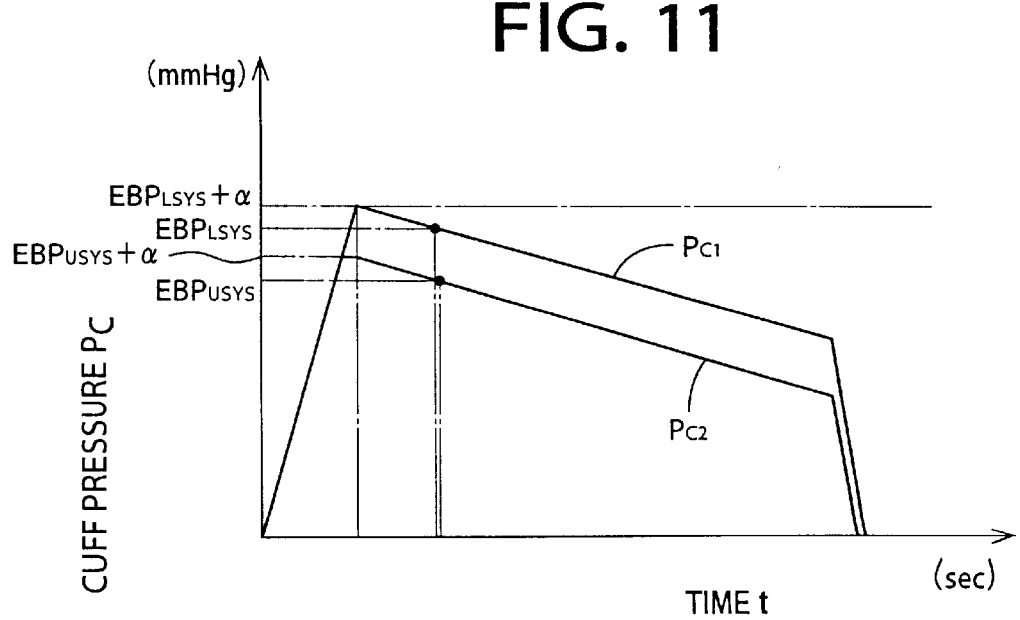
FIG. 11 is a graph showing respective changes of the respective air pressures $P_{C1}$, $P_{C2}$ of the two inflatable cuffs of the measuring apparatus of FIG. 8, with respect to time t, in the second-time BP measuring operation in which respective pressures at which respective decreasings of the two air pressures $P_{C1}$, $P_{C2}$ are started, are adjusted relative to each other.
Figure 12:
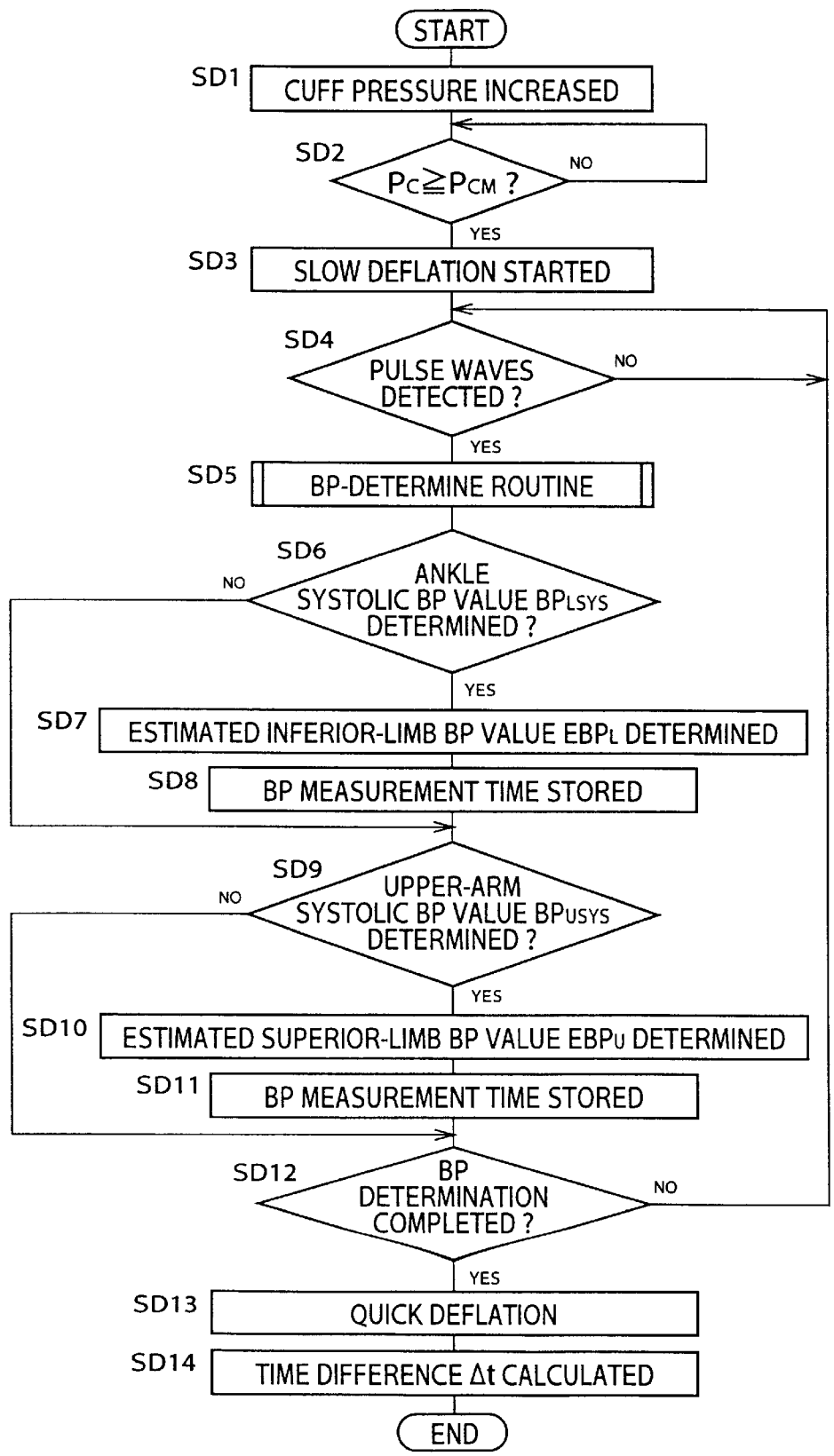
FIG. 12 is a flow chart representing an initial-time BP-measure routine according to which the control device of the measuring apparatus of FIG. 8 is operated to carry out an initial-time BP measuring operation.
Figure 13:
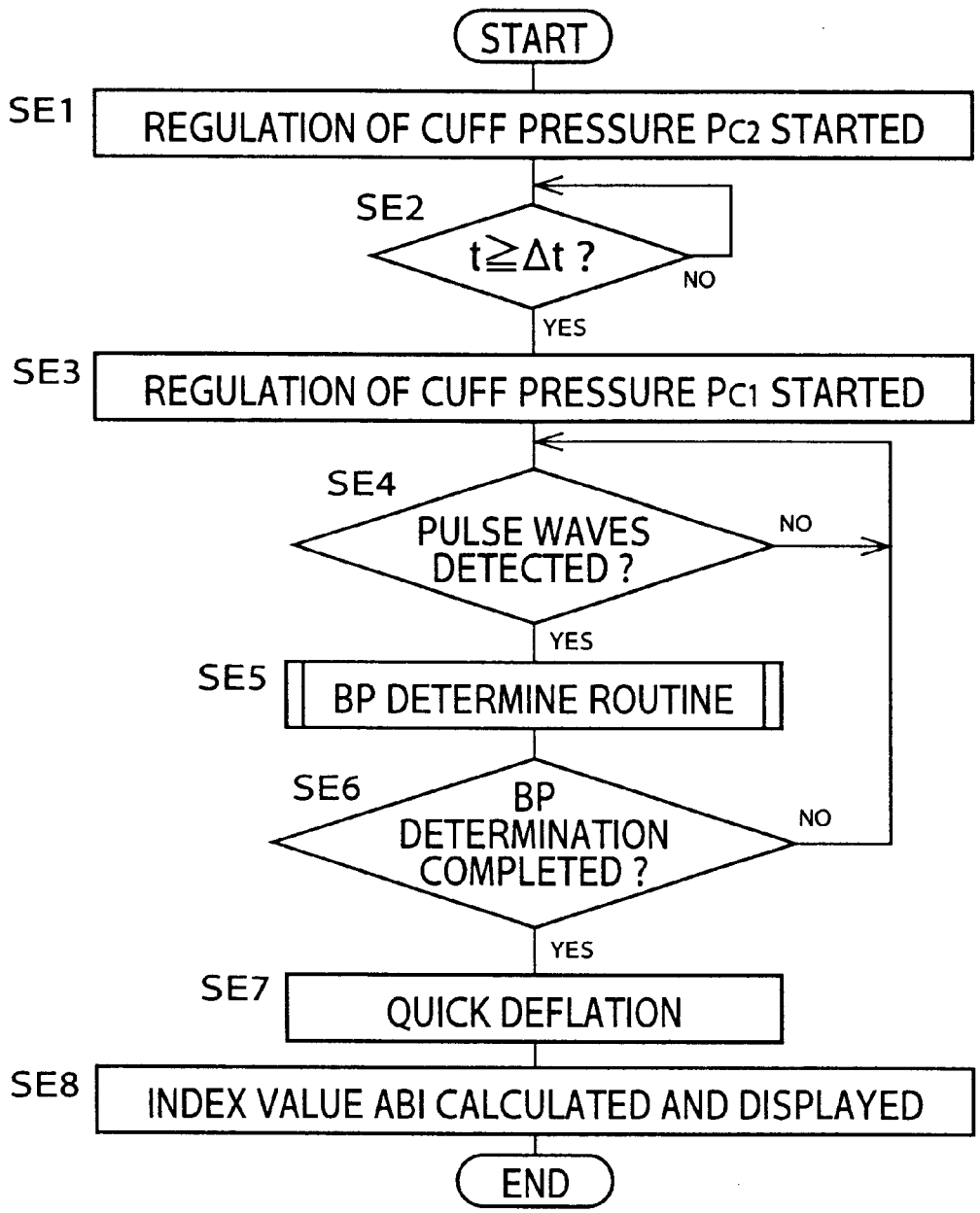
FIG. 13 is a flow chart representing a second-time BP-measure routine according to which the control device of the measuring apparatus of FIG. 8 is operated to carry out the second-time BP measuring operation.

FIG. 8 is a diagrammatic view showing the construction of the measuring apparatus 210. The ankle/arm BP index measuring apparatus 210 is a sort of superior-and-inferior-limb ("SIL") BP index measuring apparatus, since the measuring apparatus 210 measures, as an inferior-limb BP value, a BP value from an ankle of a patient as a living person and measures, as a superior-limb BP value, a BP value from an upper arm of the patient. The present apparatus 210 carries out the BP measurements on the patient who takes his or her face-down, lateral, or face-up position so that the upper arm and the ankle are substantially level with each other.

In FIG. 8, the ankle/arm BP index measuring apparatus 210 includes an ankle BP measuring device 216 as an inferior-limb BP measuring device which measures a BP value from an ankle 212 (e.g., a right ankle) of the patient, and an upper-arm BP measuring device 218 as a superior-limb BP measuring device which measures a BP value from an upper arm 214 of the patient.

The ankle BP measuring device 216 includes an inflatable cuff 220 which includes a belt-like cloth bag and a rubber bag accommodated in the cloth bag and which is wound around the ankle 212 of the patient; a piping 222; and a pressure sensor 224, an electrically-operated switch valve 226, and an air pump 228 which are connected to the cuff 220 via the piping 222. The switch valve 226 is selectively placed in one of three operation states, that is, (a) a pressurized-air-supply state in which the switch valve 226 allows pressurized air to be supplied from the air pump 228 to the cuff 220, (b) a slow-deflation state in which a degree of opening of the switch valve 226 is so controlled as to allow the pressurized air to be deflated slowly at an arbitrary rate from the cuff 220, and (c) a quick-deflation state in which the switch valve 226 allows the pressurized air to be deflated quickly from the cuff 220.

The pressure sensor 224 detects an air pressure in the cuff 220, and supplies a pressure signal, $SP_1$, representing the detected air pressure, to a static-pressure filter circuit 230 and a pulse-wave filter circuit 232. The static-pressure filter circuit 230 includes a low-pass filter which allows only low frequencies to pass therethrough and thereby selects, from the pressure signal $SP_1$, a cuff-pressure signal, $SK_1$, representing a cuff pressure, $P_{C1}$, as the constant component of the detected air pressure. The filter circuit 230 supplies the cuff-pressure signal $SK_1$ to an electronic control device 236 via an analog-to-digital ("A/D") converter 234.

The pulse-wave filter circuit 232 includes a band-pass filter which allows only specific frequencies to pass therethrough and thereby selects, from the pressure signal $SP_1$, a pulse-wave signal, $SM_1$, representing a pulse wave as the oscillatory component of the detected air pressure. The filter circuit 232 supplies the pulse-wave signal $SM_1$ to the control device 236 via an A/D converter 238.

The upper-arm BP measuring device 218 includes an inflatable cuff 240, a piping 242, a pressure sensor 244, and a switch valve 246 which have respective constructions identical with those of the counterparts 220, 222, 224, 226 of the ankle BP measuring device 216. The cuff 240 is wound around the upper arm 214, and the switch valve 246 is connected to the air pump 228. The pressure sensor 244 detects an air pressure in the cuff 240, and supplies a pressure signal, $SP_2$, representing the detected air pressure, to a static-pressure filter circuit 248 and a pulse-wave filter circuit 250 which have respective constructions identical with those of the counterparts 230, 232 of the ankle BP measuring device 216. The static-pressure filter circuit 248 selects, from the pressure signal $SP_2$, a cuff-pressure signal, $SK_2$, representing a cuff pressure, $P_{C2}$, as the constant component of the detected air pressure, and supplies the cuff-pressure signal $SK_2$ to the control device 236 via an A/D converter 252. The pulse-wave filter circuit 250 selects, from the pressure signal $SP_2$, a pulse-wave signal, $SM_2$, representing a pulse wave as the oscillatory component of the detected air pressure, and supplies the pulse-wave signal $SM_2$ to the control device 236 via an A/D converter 254.

The electronic control device 236 is essentially provided by a microcomputer including a central processing unit ("CPU") 256, a read only memory ("ROM") 258, a random access memory ("RAM") 260, and an input-and-output ("I/O") port (not shown), and processes input signals according to control programs pre-stored in the ROM 258, while utilizing the temporary-storage function of the RAM 260. The control device 236 outputs, from the I/O port, drive signals to the air pump 228 and the two switch valves 226, 246 to control the respective operations thereof, and display signals to a display device 262 to control the contents displayed thereby.

FIG. 2 is a diagrammatic view for explaining the important control functions of the control device 236.

A first cuff-pressure changing or regulating means 270 regulates, before a proper-inferior-limb-BP determining means 278 and a proper-superior-limb-BP determining means 280, described below, determine a proper inferior-limb BP value and a proper superior-limb BP value, the air pump 228 and the two switch valves 226, 246, so as to change the respective air pressures $P_{C1}$, $P_{C2}$ of the two cuffs 220, 240 while keeping the two air pressures $P_{C1}$, $PC_2$ substantially equal to each other. For example, the first cuff-pressure regulating means 270 simultaneously switches the two switch valves 226, 246 to their pressurized-air-supply positions, so that the respective air pressures $P_{C1}$, $P_{C2}$ of the two cuffs 220, 240 are quickly increased up to a predetermined target pressure value, $P_{CM}$, (e.g., about 180 mmHg), and then simultaneously switches the two switch valves 226, 246 to their slow-deflation positions, so that the two air pressures $P_{C1}$, $P_{C2}$ are slowly decreased at a rate of about 3 mmHg/sec.

An estimated-inferior-limb-BP determining means 272 determines respective amplitudes of heartbeat-synchronous pulses of an anterior- or posterior-tibial-artery pulse wave (hereinafter, referred to as the "tibial-artery pulse wave") represented by the pulse-wave signal $SM_1$ obtained by the pulse-wave filter circuit 232 when the air pressure $P_{C1}$ of the cuff 220 wound around the ankle 212 is slowly changed by the first cuff-pressure regulating means 270, and determines a plurality of sorts of ankle BP values, $BP_L$ (ankle systolic BP value, $BP_{LSYS}$, ankle diastolic BP value, $BP_{LDIA}$, etc.), each as a BP value of the ankle 212, according to well-known oscillometric method, based on the timewise change of the thus determined respective pulse amplitudes. In addition, the estimated-inferior-limb-BP determining means 272 determines, as an estimated inferior-limb BP value, $EBP_L$, one of the thus determined ankle BP values $BP_L$ that is preferably of the same sort as that of a proper inferior-limb BP value which is used by an ankle/arm BP index determining means 282, described later, to determine an ankle/arm BP index value (hereinafter, referred to as the "ABI" value).

An estimated-superior-limb-BP determining means 274 determines respective amplitudes of heartbeat-synchronous pulses of a brachial-artery pulse wave represented by the pulse-wave signal $SM_2$ obtained by the pulse-wave filter circuit 250 when the air pressure $P_{C2}$ of the cuff 240 wound around the upper arm 214 is slowly changed by the first cuff-pressure regulating means 270, and determines a plurality of sorts of upper-arm BP values, $BP_U$ (upper-arm systolic BP value, $BP_{USYS}$, upper-arm diastolic BP value, $BP_{UDIA}$, etc.), each as a BP value of the upper arm 214, according to the oscillometric method, based on the timewise change of the thus determined respective pulse amplitudes. In addition, the estimated-superior-limb-BP determining means 274 determines, as an estimated superior-limb BP value, $EBP_U$, one of the thus determined upper-arm BP values $BP_U$ that is of the sort corresponding to that of the one ankle BP value $BP_U$ determined as the estimated inferior-limb BP value $EBP_L$ by the estimated-inferior-limb-BP determining means 272. For example, in the case where the ankle systolic BP value $BP_{LSYS}$ is determined as the estimated inferior-limb BP value $EBP_L$ by the estimated-inferior-limb-BP determining means 272, the upper-arm systolic BP value $BP_{USYS}$ is determined as the estimated superior-limb BP value $EBP_U$ by the estimated-superior-limb-BP determining means 274.

A second cuff-pressure changing or regulating means 276 includes an inferior-limb cuff-pressure regulating means which controls the air pump 228 and the switch valve 226, so that the air pressure $P_{C1}$ of the cuff 220 is first quickly increased up to a predetermined target pressure value lower than the diastolic BP value of the patient and then slowly increased at, e.g., a rate of about 3 mmHg/sec, or so that the air pressure $P_{C1}$ of the cuff 220 is quickly increased up to a predetermined target pressure value higher than the systolic BP value of the patient. In addition, the second cuff-pressure regulating means 276 includes a superior-limb cuff-pressure regulating means which controls the air pump 228 and the switch valve 246, so that the air pressure $P_{C2}$ of the cuff 240 is first quickly increased up to a predetermined target pressure value lower than the diastolic BP value of the patient and then slowly increased at, e.g., a rate of about 3 mmHg/sec, or so that the air pressure $P_{C2}$ of the cuff 240 is quickly increased up to a predetermined target pressure value higher than the systolic BP value of the patient. In each case, subsequently, the cuff pressure $P_{C2}$ is slowly decreased at, e.g., a rate of about 3 mmHg/sec. Moreover, the second cuff-pressure regulating means 276 includes a cuff-pressure adjusting means which controls the two switch valves 226, 246, and thereby changes the respective cuff pressures $P_{C1}$, $P_{C2}$ of the two cuffs 220, 240, such that a time when the cuff pressure $P_{C1}$ being slowly changed by the inferior-limb cuff-pressure regulating means becomes equal to the estimated inferior-limb BP value $EBP_L$ determined by the means 272 coincides with a time when the cuff pressure $P_{C2}$ being slowly changed by the superior-limb cuff-pressure regulating means becomes equal to the estimated superior-limb BP value $EBP_U$ determined by the means 274. In the above-indicated first case where the air pressures $P_{C1}$, $P_{C2}$ of the cuffs 220, 240 are first quickly increased up to the predetermined target pressure value lower than the diastolic BP value of the patient and then slowly increased at respective low rates, the cuff-pressure adjusting means adjusts at least one of respective timings at which the slow increasing of the cuff pressures $P_{C1}$, $P_{C2}$ is started and the respective low rates at which the cuff pressures $P_{C1}$, $P_{C2}$ are slowly increased. In the above-indicated second case where the air pressures $P_{C1}$, $P_{C2}$ of the cuffs 220, 240 are first quickly increased up to respective predetermined target pressure values higher than the systolic BP value of the patient and then decreased at respective low rates, the cuff-pressure adjusting means adjusts at least one of respective timings at which the slow decreasing of the cuff pressures $P_{C1}$, $P_{C2}$ is started, the respective predetermined target pressure values at which the slow decreasing of the cuff pressures $P_{C1}$, $P_{C2}$ is started, and the respective low rates at which the cuff pressures $P_{C1}$, $P_{C2}$ are slowly decreased.

FIGS. 3 and 4 shows two different manners in which the second cuff-pressure regulating means 276 controls the two switch valves 226, 246 and thereby changes the two cuff pressures $P_{C1}$, $P_{C2}$ and in each of which the estimated inferior and superior systolic BP values $EBP_{LSYS}$, $EBP_{USYS}$ are used as the estimated inferior and superior BP values $EBP_L$, $EBP_U$. More specifically described, FIG. 3 shows the first manner in which the two cuff pressures $P_{C1}$, $P_{C2}$ are increased at the same rate, decreased from the same pressure, and decreased at the same rate, but the respective timings at which the respective increasing (accordingly, decreasing) of the two pressures $P_{C1}$, $P_{C2}$ is started are adjusted relative to each other, and FIG. 4 shows the second manner in which the two cuff pressures $P_{C1}$, $P_{C2}$ are increased at the same timing, increased at the same rate, decreased at the same timing, and decreased at the same rate, but the respective pressures from which the two pressures $P_{C1}$, $P_{C2}$ are decreased are adjusted relative to each other. That is, the cuff pressure $P_{C1}$ is decreased from a value greater than the estimated inferior-limb systolic BP value $EBP_{LSYS}$ by a value, α, which is experimentally determined in advance and the cuff pressure $P_{C2}$ is decreased from a value greater than the estimated superior-limb systolic BP value $EBP_{USYS}$ by the value α.

The proper-inferior-limb BP determining means 278 determines respective amplitudes of heartbeat-synchronous pulses of the tibial-artery pulse wave represented by the pulse-wave signal $SM_1$ obtained when the air pressure $P_{C1}$ is slowly changed by the second cuff-pressure regulating means 276, and determines a plurality of sorts of ankle BP values, $BP_L$ (ankle systolic BP value $BP_{LSYS}$, ankle diastolic BP value $BP_{LDIA}$, etc.), each as a BP value of the ankle 212, according to the well-known oscillometric method, based on the timewise change of the thus determined respective pulse amplitudes.

The proper-superior-limb BP determining means 280 determines respective amplitudes of heartbeat-synchronous pulses of the brachial-artery pulse wave represented by the pulse-wave signal $SM_2$ obtained when the air pressure $P_{C2}$ is slowly changed by the second cuff-pressure regulating means 276, and determines a plurality of sorts of upper-arm BP values $BP_U$ (upper-arm systolic BP value $BP_{USYS}$, upper-arm diastolic BP value $BP_{UDIA}$, etc.), each as a BP value of the upper arm 214, according to the well-known oscillometric method, based on the timewise change of the thus determined respective pulse amplitudes.

The ankle/arm BP index determining means 282 determines or calculates an ankle/arm BP index ("ABI") value based on the ankle BP value $BP_L$ determined by the proper-inferior-limb BP determining means 278 and the corresponding upper-arm BP value $BP_U$ determined by the proper-superior-limb BP determining means 28 (e.g., the proper superior-limb systolic BP value $BP_{USYS}$ corresponds to the proper inferior-limb systolic BP value $BP_{LSYS}$, and the proper superior-limb diastolic BP value $BP_{UDIA}$ corresponds to the proper inferior-limb diastolic BP value $BP_{LDIA}$). For example, the API value may be obtained by dividing the proper inferior-limb BP value $BP_L$ by the corresponding proper superior-limb BP value $BP_U$, or dividing the proper superior-limb BP value $BP_U$ by the corresponding proper inferior-limb BP value $BP_L$. The thus determined API value is displayed on the display device 62.

FIGS. 5 and 6 are flow charts representing control programs according to which the control device 236 is operated. FIG. 5 shows the flow chart representing the initial-time BP-measure routine, and FIG. 6 shows the flow chart representing the second-time BP-measure routine.

First, the control device 38 carries out Steps SD1, SD2, and SD3 of FIG. 5 corresponding to the first cuff-pressure regulating means 270. At Step SD1, the two switch valves 226, 246 are simultaneously switched to their pressurized-air-supply positions and the air pump 228 is operated, so that the respective air pressures of the two cuffs 220, 240 are quickly increased at the same rate. This is indicated by a time, $t_0$, shown in FIG. 14A.

At the following step, Step SD2, it is judged whether both the air pressures $P_{C1}$, $P_{C2}$ of the two cuffs 220, 240 have reached the predetermined target pressure value $P_{CM}$ (about 180 mmHg). If a negative judgment is made at Step SD2, Steps SD1 and SD2 are repeated to continue increasing the cuff pressures $P_{C1}$, $P_{C2}$.

If a positive judgment is made at Step SD2, the control goes to Step SD3 to stop the operation of the airpump 228 and simultaneously switch the two switch valves 226, 246 to their slow-deflation positions, so that the respective air pressures of the two cuffs 220, 240 are decreased slowly at the predetermined low rate of about 3 mmHg/sec. This is indicated by a time, $t_1$, shown in FIG. 14A.

Figure 14A:
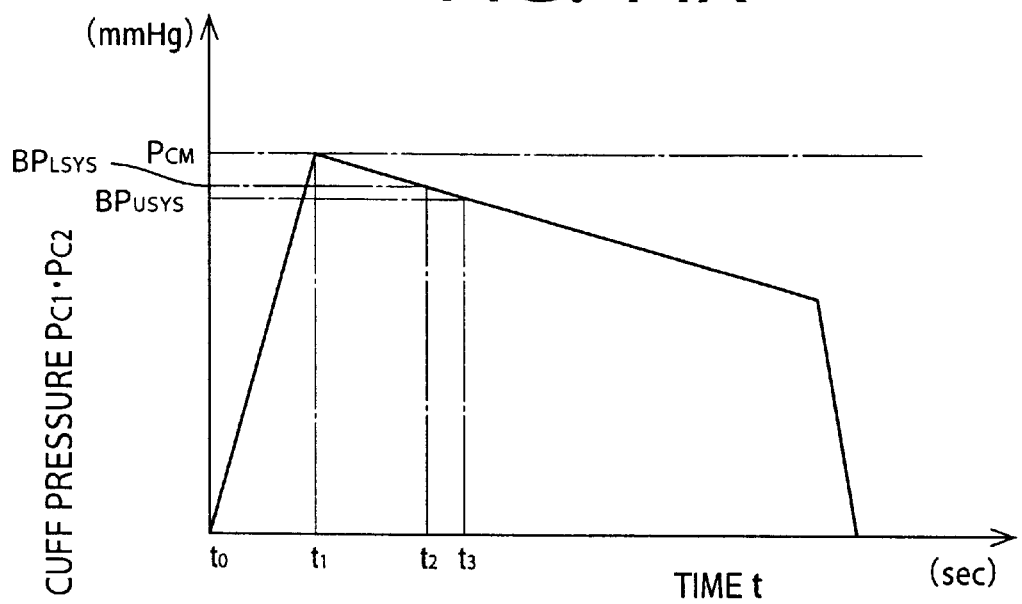
FIG. 14A is a graph showing respective changes of the respective air pressures $P_{C1}$, $P_{C2}$ of the two inflatable cuffs of the measuring apparatus of FIG. 8, with respect to time t, in the initial-time BP measuring operation.
Figure 14B:
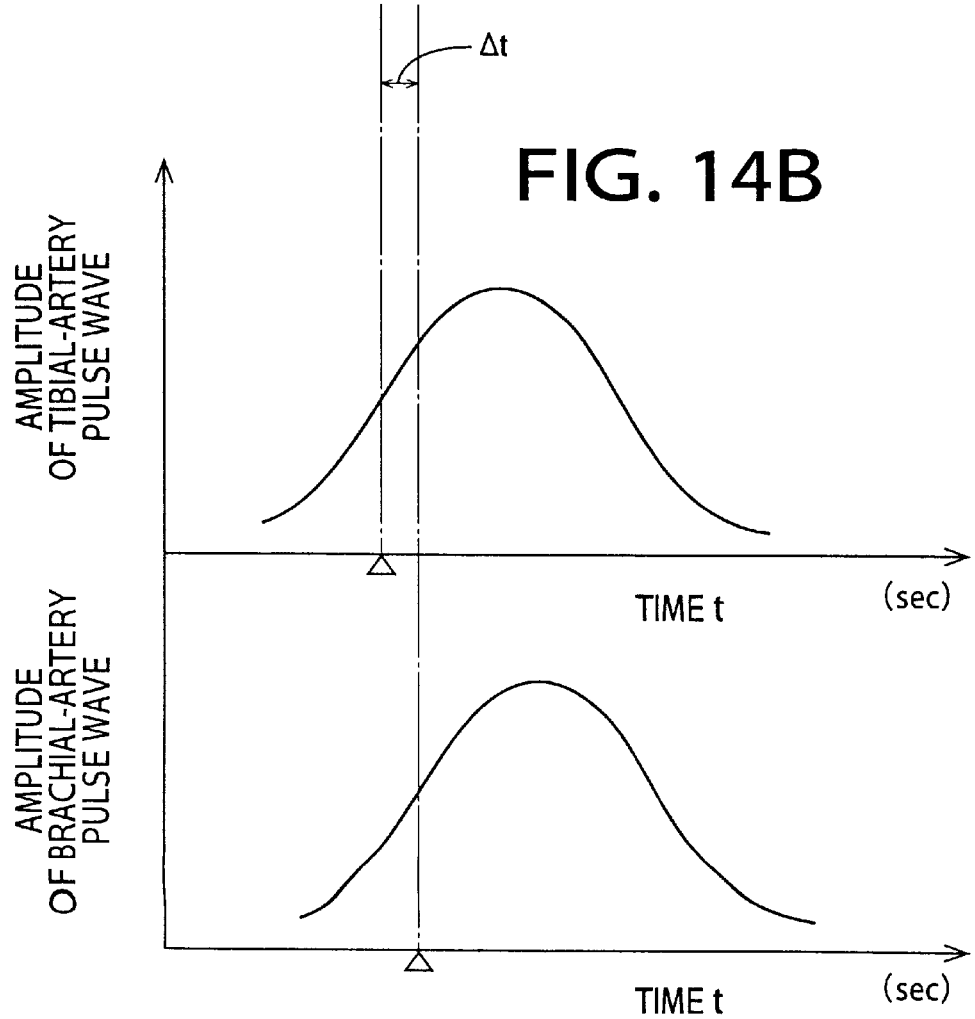
FIG. 14B shows two graphs an upper one of which represents a timewise change of respective amplitudes of heartbeat-synchronous pulses of a tibial-artery pulse wave, in the initial-time BP measuring operation, and the other, lower one of which represents a timewise change of respective amplitudes of heartbeat-synchronous pulses of a brachial-artery pulse wave, in the initial-time BP measuring operation.

Step SD3 is followed by Step SD4 to read in the pulse-wave signals $SM_1$, $SM_2$ supplied from the pulse-wave filter circuits 232, 250 and judge whether the two filter circuits have detected respective one heartbeat-synchronous pulses of the tibial-artery pulse wave and the brachial-artery pulse wave. If a negative judgment is made at Step SD4, the control device 236 repeats Step SD4. Meanwhile, if a positive judgment is made, the control, of the control device 236 goes to the BP-determine routine of Step SD5. More specifically described, the control device 236 determines an amplitude (i.e., a peak magnitude) of the detected one heartbeat-synchronous pulse of the tibial-artery pulse wave, and an amplitude of the detected one heartbeat-synchronous pulse of the brachial-artery pulse wave. In addition, the control device 236 determines an ankle BP value $BP_L$ based on the time-wise change of the determined amplitudes according to a well-known oscillometric BP-determine algorithm. Similarly, the control device 236 determines an upper-arm BP value $BP_U$ based on the time-wise change of the determined amplitudes according to the oscillometric BP-determine algorithm. FIG. 14B shows the time-wise change (i.e., envelope) of the amplitudes of the tibial-artery pulse wave, and the time-wise change of the amplitudes of the brachial-artery pulse wave, each determined at Step SD5. Moreover, the control device 236 stores, in the RAM 260, not only the thus determined BP values $BP_L$, $BP_U$, but also the respective rates of change of the cuff pressures $P_{C1}$, $P_{C2}$ of the two cuffs 220, 240 connected to the two switch valves 226, 246. Those rates of change of cuff pressures $P_{C1}$, $P_{C2}$ of the two cuffs 220, 240 are defined by respective degrees of opening of the two switch valves 226, 246, respectively.

Step SD5 is followed by Step SD6 to judge whether the ankle BP measuring device 216 have measured or determined an ankle systolic BP value $BP_{LSYS}$ at Step SD5. If a negative judgment is made at Step SD6, the control of the control device 236 skips Steps SD7 and SD8 and goes to Step SD9. On the other hand, if a positive judgment is made at Step SD6, the control goes to Step SD7 to determine the ankle systolic BP value $BP_{LSYS}$ determined at Step SD5, as the estimated inferior-limb systolic BP value $EBP_{LSYS}$. Thus, Steps SD5, SD6 and SD7 correspond to the estimated-inferior-limb BP determining means 272. At the following step, Step SD8, the control device 236 stores, in the RAM 260, a time when the ankle systolic BP value $BP_{LSYS}$ is determined at Step SD5. This time is substantially equal to a time when the ankle systolic BP value $BP_{LSYS}$ is measured by the pressure sensor 224. This is indicated by a time, $t_2$, shown in FIG. 14A.

If a negative judgment is made at Step SD6, or after Step SD8, the control goes to Step SD9 to judge whether the upper-arm BP measuring device 218 have measured or determined an upper-arm systolic BP value $BP_{USYS}$ at Step SD5. If a negative judgment is made at Step SD9, the control of the control device 236 skips Steps SD10 and SD11 and goes to Step SD12. On the other hand, if a positive judgment is made at Step SD9, the control goes to Step SD10 to determine the upper-arm systolic BP value $B_{USYS}$ determined at Step SD5, as the estimated superior-limb systolic BP value $EBP_{USYS}$. Thus, Steps SD5, SD9 and SD10 correspond to the estimated-superior-limb BP determining means 274. At the following step, Step SD11, the control device 236 stores, in the RAM 260, a time when the upper-arm systolic BP value $BP_{USYS}$ is determined at Step SD5. This time is substantially equal to a time when the upper-arm systolic BP value $BP_{USYS}$ is measured by the pressure sensor 244. This is indicated by a time, $t_3$, shown in FIG. 14A. FIG. 14A shows an example in which the ankle systolic BP value $BP_{LSYS}$ is measured prior to the upper-arm systolic BP value $BP_{USYS}$, that is, the former BP value $BP_{LSYS}$ is higher than the latter BP value $BP_{USYS}$.

If a negative judgment is made at Step SD9, or after Step SD11, the control goes to Step SD12 to judge whether the ankle and upper-arm BP measuring device 216, 218 have measured or determined ankle and upper-arm diastolic BP values $BP_{LDIA}$, $BP_{UDIA}$ at Step SD5. If a negative judgment is made at Step SD12, the control repeats Steps SD4 to SD12 while determining the amplitude of each of successive heartbeat-synchronous pulses of the tibial-artery pulse wave and the amplitude of each of successive heartbeat-synchronous pulses of the brachial-artery pulse wave and trying to complete the BP-determine routine based on the successively updated timewise changes of amplitudes of the tibial-artery and brachial-artery pulse waves.

If a positive judgment is made at Step SD12, the control of the control device 236 goes to Step SD13 corresponding to the first cuff-pressure regulating means 270. At Step SD13, the two switch valves 226, 246 are switched to their quick-deflation positions, so that the respective air pressures of the two cuffs 220, 240 are quickly decreased.

Step SD13 is followed by Step SD14 to determine a time difference, $\Delta t$, between the time $t_2$ stored at Step SD8 and the time $t_3$ stored at Step SD10, that is, between the time when the ankle systolic BP value $BP_{LSYS}$ is measured and the time when the upper-arm systolic BP value $BP_{USYS}$ is measured. The time difference $\Delta t$ is stored in the RAM 260. Thus, the initial-time BP-measure routine is finished.

After quitting the initial-time BP-measure routine of FIG. 5, the control device 236 enters the second-time BP-measure routine of FIG. 6, after a predetermined time such as about 10 seconds has passed after the end of the routine of FIG. 5. FIG. 6 shows the control program according to which the cuff pressures $P_{C1}$, $P_{C2}$ are changed in the first exemplary manner, shown in FIG. 3, so that a time when the cuff pressure $P_{C1}$ becomes equal to the estimated inferior-limb systolic BP value $EBP_{LSYS}$ determined at Step SD 7 coincides with a time when the cuff pressure $PC_2$ becomes equal to the estimated superior-limb systolic BP value $EBP_{USYS}$ determined at Step SD10. FIG. 3 shows the case where at Step SD5 the estimated inferior-limb systolic BP value $EBP_{LSYS}$ is determined as being higher than the estimated superior-limb systolic BP value $EBP_{USYS}$.

First, the control device 236 carries out Steps SE1 to SE3 corresponding to the second cuff-pressure regulating means 276. At Step SE1, the control device 236 starts regulating one of the two cuff pressures $P_{C1}$, $P_{C2}$ that corresponds to the lower one of the estimated inferior-limb and superior-limb systolic BP values $EBP_{LSYS}$, $EBP_{USYS}$. In the example shown in FIG. 3, the control device 236 first starts regulating the cuff pressure $P_{C2}$. More specifically described, the air pump 228 is operated, and the switch valve 246 is switched to its pressurized-air-supply position, so that the quick increasing of the cuff pressure $P_{C2}$ is started at the time $t_0$. After the cuff pressure $P_{C2}$ is quickly increased up to the predetermined target pressure value $P_{CM}$ (e.g., 180 mmHg), the switch valve 246 is switched to its slow-deflation position, so that the cuff pressure $P_{C2}$ is decreased slowly at the predetermined rate (e.g. 3 mmHg/sec). The degree of opening of the switch valve 246, employed in the second-time BP measuring operation, is determined according to a relationship between the degree of opening of the switch valve 246 and the rate of change of the cuff pressure $P_{C2}$, stored in the RAM 260 in the initial-time BP measuring operation. Thus, the cuff pressure $P_{C2}$ can be decreased accurately at the predetermined target low rate.

Step SE, is followed by Step SE2 to judge whether the time t that is measured from the time $t_0$ when the increasing of the cuff pressure $P_{C2}$ is started at Step SE1, has elapsed by the time difference $\Delta t$ determined at Step SD14 of FIG. 5. If a negative judgment is made at Step SE2, Step SE2 is repeated to continue changing the cuff pressure $P_{C2}$ only. Meanwhile, if a positive judgment is made at Step SE2, the control of the control device 236 goes to Step SE3 to start regulating the cuff pressure $P_{C1}$ of the cuff 220, like the cuff pressure $P_{C2}$ of the cuff 240. That is, the switch valve 226 is switched to its pressurized-air-supply position, so that the increasing of the cuff pressure $P_{C1}$ is started at the time $t_1$ shown in FIG. 3. The cuff pressure $P_{C1}$ is quickly increased up to the same target pressure value $P_{CM}$ up to which the cuff pressure $P_{C2}$ is increased, at the same rate as that at which the cuff pressure $P_{C2}$ is increased. Thereafter, the switch valve 226 is switched to its slow-deflation position, so that the cuff pressure $P_{C1}$ is decreased slowly at the same rate as that at which the cuff pressure $P_{C2}$ is decreased. The degree of opening of the switch valve 226, used in the second-time BP measuring operation, is determined based on the rate of change of the cuff pressure $P_{C1}$, according to a relationship between the degree of opening of the switch valve 226 and the rate of change of the cuff pressure $P_{C1}$, stored in the RAM 260 in the initial-time BP measuring operation. Thus, the cuff pressure $P_{C1}$ can be decreased accurately at the predetermined target low rate.

Step SE3 is followed by Step SE4 where the control device 236 reads in the pulse-wave signals $SM_1$, $SM_2$ and judge whether the control device 236 have read in respective one heartbeat-synchronous pulses of the tibial-artery and brachial-artery pulse waves. If a negative judgment is made at Step SE3, the control device 236 repeats this step. Meanwhile, if a positive judgment is made, the control goes to Step SE5 corresponding to the proper inferior-limb and superior-limb BP determining means 278, 280. At Step SE5, the control device 236 determines respective amplitudes of successive heartbeat-synchronous pulses of the tibial-artery pulse wave, and determines a proper ankle BP value $BP_L$ such as an ankle systolic BP value $BP_{LSYS}$ based on the timewise change of the thus determined amplitudes. In addition, the control device 236 determines respective amplitudes of successive heartbeat-synchronous pulses of the brachial-artery pulse wave, and determines a proper upper-arm BP value $BP_U$ such as an upper-arm systolic BP value $BP_{USYS}$ based on the timewise change of the thus determined amplitudes.

At the following step, Step SE6, the control device 236 judges whether the BP determination at Step SE5 has been completed. If a positive judgment is made at Step SE6, the control goes to Step SB7 corresponding to the second cuff-pressure regulating means 276, and quickly deflates the two cuffs 220, 240.

Step SE7 is followed by Step SE8 corresponding to the ankle/arm BP index determining means 282. At Step SE8, the control device 236 calculates an ankle/arm BP index ("ABI") value by dividing the proper ankle systolic BP value $BP_{LSYS}$ determined at Step SE5 by the proper upper-arm systolic BP value $BP_{USYS}$ determined at Step SE5. The thus determined ABI value is displayed on the display device 262.

In the second embodiment, the second cuff-pressure regulating means 276 (Steps SE1 to SE3) regulates or changes, in the second-time BP measuring operation, the cuff pressures $P_{C1}$, $P_{C2}$ such that the time when the cuff pressure $P_{C1}$ becomes, while being slowly decreased, equal to the estimated inferior-limb systolic BP value $EBP_{LSYS}$ coincides with the time when the cuff pressure $P_{C2}$ becomes, while being slowly decreased, equal to the estimated superior-limb systolic BP value $EBP_{USYS}$. While the second cuff-pressure regulating means 276 changes the cuff pressures $P_{C1}$, $P_{C2}$ in this manner, the ankle BP measuring device 216 measures an ankle systolic BP value $BP_{LSYS}$, and the upper-arm BP measuring device 218 measures an upper-arm systolic BP value $BP_{USYS}$. The ankle/arm BP index determining means 282 determines or calculates an ankle/arm BP index ("ABI") value based on the thus measured ankle systolic BP value $BP_{LSYS}$ and upper-arm systolic BP value $BP_{USYS}$. Therefore, the present apparatus 210 provides highly accurate ABI values.

In addition, in the second embodiment, the estimated-inferior-limb-BP determining means 272 (SD5, SD7) determines, as the estimated inferior-limb systolic BP value $EBP_{LSYS}$, an ankle systolic BP value $BP_{LSYS}$ which is actually measured from the patient immediately before the above-indicated ABI value is determined on the patient, and the estimated-superior-limb-BP determining means 274 (SD5, SD10) determines, as the estimated superior-limb systolic BP value $EBP_{USYS}$, an upper-arm systolic BP value $BP_{USYS}$ which is actually measured from the patient immediately before the ABI value is determined on the patient. Accordingly, the present apparatus 210 can assure that the time when the ankle systolic BP value $BP_{LSYS}$ to be used to determine the ABI value is measured accurately coincides with the time when the upper-arm systolic BP value $BP_{USYS}$ to be used to determine the ABI value is measured. Thus, the present apparatus 210 can provide more highly accurate ABI values.

Moreover, in the second embodiment, the first cuff-pressure regulating means (Steps SD1 to SD3) regulates or changes, in the initial-time BP measuring operation, the cuff pressures $P_{C1}$, $PC_2$ such that the cuff pressures $P_{C1}$, $P_{C2}$ are kept substantially equal to each other as shown in FIG. 14A. Accordingly, the estimated inferior-limb systolic BP value $EBP_{LSYS}$ and the estimated superior-limb systolic BP value $EBP_{USYS}$ can be measured at respective times or timings which are considerably near to each other. This contributes to minimizing the influence of the measurement-time difference to the difference between the estimated inferior-limb systolic BP value $EBP_{LSYS}$ and the estimated superior-limb systolic BP value $EBP_{USYS}$. Thus, the present apparatus 210 can more reliably assure that the time when the ankle systolic BP value $BP_{LSYS}$ is measured accurately coincides with the time when the upper-arm systolic BP value $BP_{USYS}$ is measured.

While the present invention has been described in its preferred embodiments, it may be otherwise embodied.

For example, in the first embodiment shown in FIGS. 1 to 7, the cuff-pressure regulating means 80 controls, based on the time differences $\Delta t_{cb}$, $\Delta t_{ca}$ determined by the time-difference calculating means 86, the three switch valves 30, 46, 58 to start decreasing the respective air pressures of the three cuffs 24, 40, 52 at such respective timings which should assure that a time when a right-leg first systolic BP value $BP1_{RSYS}$ as a first systolic BP value of the right ankle 12 is measured by the right-leg first BP measuring device 14, a time when a left-leg first systolic BP value $BP_{LSYS}$ as a first systolic BP value of the left ankle 16 is measured by the left-leg first BP measuring device 18, and a time when a second systolic BP value BP2 of the upper arm 20 is measured by the second BP measuring device 22, coincide with one another. However, it is possible to select the lower one of the right-leg and left-leg first systolic BP values $BP1_{RSYS}$, $BP1_{LSYS}$ measured in the initial-time BP measuring operation, and controls, based on one of the two time differences $\Delta t_{cb}$, $\Delta t_{ca}$ that corresponds to the selected one first systolic BP value, one of the two switch valves 30, 46 that corresponds to the selected one first systolic BP value, and the switch valve 58 to start decreasing the respective air pressures of one of the two cuffs 24, 40 that corresponds to the selected one first systolic BP value, and the cuff 52, at such respective timings which should assure that a time when a first systolic BP value BP1 is measured by one of the two first BP measuring devices 14, 18 that corresponds to the selected one first systolic BP value, and a time when a second systolic BP value BP2 of the upper arm 20 is measured by the second BP measuring device 22, coincide with one another.

Although in the first embodiment the right-leg first BP value $BP1_R$ and the left-leg first BP value $BP1_L$ are measured from the right and left ankles 12, 16 of the patient, respectively, it is possible to measure only one of the two first BP values $BP1_R$, $BP1_L$.

In the second embodiment shown in FIGS. 8 to 13, 14A, and 14B, the estimated-inferior-limb-BP determining means 272 determines, as the estimated inferior-limb BP value $EBP_L$, one of the ankle BP values $BP_L$ actually measured from the patient from whom the ABI value is to be measured. However, the ankle/arm BP index measuring device 210 may be provided with an input device (not shown) which is operable by an operator for inputting the estimated inferior-limb BP value $EBP_L$. This may apply to the estimated superior-limb BP value $EBP_U$. That is, the input device may be operable by the operator for inputting the estimated superior-limb BP value $EBP_L$.

In each of the first and second embodiments, each of the right-leg first BP measuring device 14, the left-leg first BP measuring device 16, the second BP measuring device 22, the ankle BP measuring device 216, and the upper-arm BP measuring device 218 measures a BP value according to the oscillometric method. However, each of the five BP measuring devices 14, 16, 22, 216, 218 may be one which measures a BP value according to a well-known Korotkoff-sound method in which a BP value is measured based on a cuff-pressure value read at a time when Korotkoff sounds are first or last detected. Otherwise, each device 14, 16, 22, 216, 218 may be one which measures a BP value according to a supersonic Doppler method in which, while a pressure which presses an artery is changed, a supersound emitter and a supersound receiver which are provided right above the artery cooperate with each other to detect the opening and closing of the artery.

The ankle/arm BP index measuring apparatus 10, 210 is a sort of inferior-and-superior-limb BP index measuring apparatus wherein an ankle is selected as an inferior limb and an upper arm is selected as a superior limb. However, a femoral portion or a toe may be selected as an inferior limb, and a wrist or a finger may be selected as a superior limb.

It is to be understood that the present invention may be embodied with other changes, improvements, and modifications that may occur to a person skilled in the art without departing from the scope and spirit of the invention defined in the appended claims.

What is claimed is:

1. An apparatus for measuring a superior-and-inferior-limb blood-pressure index of a living subject, comprising:.

an inferior-limb blood-pressure measuring device which includes a first inflatable cuff adapted to be wound around an inferior limb of the subject, and which measures an inferior-limb blood pressure of the subject based on a first pulse wave obtained while a first pressing pressure of the first cuff is changed;

a superior-limb blood-pressure measuring device which includes a second inflatable cuff adapted to be wound around a superior limb of the subject, and which measures a superior-limb blood pressure of the subject based on a second pulse wave obtained while a second pressing pressure of the second cuff is changed;

a cuff-pressure changing device which changes the first and second pressing pressures of the first and second cuffs, such that a time when the first pressing pressure being changed becomes equal to an estimated inferior-limb blood pressure coincides with a time when the second pressing pressure being changed becomes equal to an estimated superior-limb blood pressure; and index determining means for determining the superior-and-inferior-limb blood-pressure index of the subject, based on the inferior-limb and superior-limb blood pressures measured by the inferior-limb and superior-limb blood-pressure measuring devices while the first and second pressing pressures of the first and second cuffs are changed by the cuff-pressure changing device.

2. An apparatus according to claim 1, further comprising:

estimated- inferior- limb-blood-pressure determining means for operating, before the cuff-pressure changing device changes the first and second pressing pressures of the first and second cuffs, the inferior-limb blood-pressure measuring device to measure an inferior-limb blood pressure of the subject, and determining the measured inferior-limb blood pressure as said estimated inferior-limb blood pressure; and estimated-superior- limb-blood-pressure determining means for operating, before the cuff-pressure changing device changes the first and second pressing pressures of the first and second cuffs, the superior-limb blood-pressure measuring device to measure a superior-limb blood pressure of the subject, and determining the measured superior-limb blood pressure as said estimated superior-limb blood pressure.

3. An apparatus according to claim 2, wherein the estimated-inferior-limb-blood-pressure determining means, and the estimated-superior-limb-blood-pressure determining means comprise means for operating, before the cuff-pressure changing device changes the first and second pressing pressures of the first and second cuffs, the inferior-limb and superior-limb blood-pressure measuring devices to measure the inferior-limb and superior-limb blood pressures of the subject while changing the first and second pressing pressures of the first and second cuffs such that the first and second pressing pressures are kept substantially equal to each other.

4. An apparatus according to claim 1, wherein the index determining means comprises means for determining, as the superior-and-inferior-limb blood-pressure index, a ratio of the inferior-limb blood pressure to the superior-limb blood pressure, or a ratio of the superior-limb blood pressure to the inferior-limb blood pressure.

5. An apparatus according to claim 1, wherein the cuff-pressure changing device comprises adjusting means for adjusting at least one of a first time when decreasing of the first pressing pressure of the first cuff is started and a second time when decreasing of the second pressing pressure of the second cuff is started, so that the time when the first pressing pressure being decreased becomes equal to the estimated inferior-limb blood pressure coincides with the time when the second pressing pressure being decreased becomes equal to the estimated superior-limb blood pressure.

6. An apparatus according to claim 5, wherein said adjusting means comprises means for adjusting at least one of a first time when increasing of the first pressing pressure of the first cuff is started and a second time when increasing of the second pressing pressure of the second cuff is started, so that the time when the first pressing pressure being decreased becomes equal to the estimated inferior-limb blood pressure coincides with the time when the second pressing pressure being decreased becomes equal to the estimated superior-limb blood pressure.

7. An apparatus according to claim 1, wherein the cuff-pressure changing device comprises adjusting means for adjusting at least one of a first pressure at which decreasing of the first pressing pressure of the first cuff is started and a second pressure at which decreasing of the second pressing pressure of the second cuff is started, so that the time when the first pressing pressure being decreased becomes equal to the estimated inferior-limb blood pressure coincides with the time when the second pressing pressure being decreased becomes equal to the estimated superior-limb blood pressure.

* * * * *